US007750033B2

(12) United States Patent
Yoshimura et al.

(10) Patent No.: US 7,750,033 B2
(45) Date of Patent: Jul. 6, 2010

(54) PREVENTIVE AND REMEDY FOR COLLAGEN OR ELASTIN METABOLIC DISORDER

(75) Inventors: Koichi Yoshimura, Yamaguchi (JP); Hiroki Aoki, Yamaguchi (JP); Masunori Matsuzaki, Yamaguchi (JP)

(73) Assignee: Yamaguchi University, Yamaguchi-shi (JP)

( * ) Notice: Subject to any disclaimer, the term of this patent is extended or adjusted under 35 U.S.C. 154(b) by 0 days.

(21) Appl. No.: 11/574,206

(22) PCT Filed: Aug. 24, 2005

(86) PCT No.: PCT/JP2005/015323

§ 371 (c)(1),
(2), (4) Date: Feb. 23, 2007

(87) PCT Pub. No.: WO2006/022281

PCT Pub. Date: Mar. 2, 2006

(65) Prior Publication Data

US 2007/0248944 A1 Oct. 25, 2007

(30) Foreign Application Priority Data

Aug. 24, 2004 (JP) ............................. 2004-244316
Feb. 14, 2005 (JP) ............................. 2005-035769

(51) Int. Cl.
*A61K 31/41* (2006.01)
*A61K 31/015* (2006.01)
(52) U.S. Cl. ...................................... 514/406; 514/765
(58) Field of Classification Search ........................ None
See application file for complete search history.

(56) References Cited

FOREIGN PATENT DOCUMENTS

WO    WO 02/085396 A1    10/2002

OTHER PUBLICATIONS

Hindershot et al., "Protein-specific chaperones: The role of hsp47 begins to gel", 2000, Current Biology, vol. 10(24), pp. R912-R915.*
Koichi Yoshimura, et al., "C-Jun N-Terminal Kinase Regulates Pathological Extracellular Matrix Metabolism in Abdominal Aortic Aneurysm in Vivo", Journal of Molecular and Cellular Cardiology, vol. 37, No. 1, p. 222, 2004, (Abstract No. B38 only).
Koichi Yoshimura, et al., "C-Jun N-Terminal Kinase Governs Pathological Extracellular Matrix Metabolism in Human Abdominal Aortic Aneurysm", Circulation, vol. 108, No. 17, p. IV-193, 2003.
Nobuya Zenpo, et al., "Antisense MT1-MMP and MMP-9 Oligonucleotides Suppress Smooth Muscle Cell Proliferation in Vitro and Aneurysmal Formation in Vivo", Myakukangaku, vol. 42, No. 6, pp. 369-374, 2002. (with partial English translation).
M. Shin, et al., "An Inhibitor of C-Jun Aminoterminal Kinase (SP600125) Represses C-Jun Activation, DNA-Binding and PMA-Inducible 92-kDA type IV Collogenase Expression", Biochimica Et Biophysica Acta, vol. 1589, No. 3, pp. 311-316, 2002.

Atsushi Masamune, et al., "A C-Jun NH2-Terminal Kinase Inhibitor SP600125 (Anthra[1, 9-cd] Pyrazole-6(2H-One) Blocks Activation of Pancreatic Stellate Cells", The Journal of Pharmacology and Experimental Therapeutics, vol. 310, No. 2, pp. 520-527, 2004.
B. Timothy Baxter, et al., "Prolonged Administration of Doxycycline in Patients With Small Asymptomatic Abdominal Aortic Aneurysms: Report of a Prospective (Phase II) Multicenter Study", Journal of Vascular Surgery, vol. 36, pp. 1-12, 2002.
Koichi Yoshimura, et al., "OE-096. C-Jun N-Terminal is Required for Development of Abdominal Aortic Aneurysm in Vivo", Circulation Journal, vol. 68, Supplement 1, 2004.
Koichi Yoshimura, et al., "SF-043-4. Future Therapy for Aortic Aneurysm Involving Molecular Targeting of C-Jun N-Terminal Kinase", Journal of Japan Surgical Society, p. 237, 2004. (with English abstract).
B. Timothy Baxter, "Could Medical Intervention Work for Aortic Aneurysms?", The American Journal of Surgery, vol. 188, pp. 628-632, 2004.
Mark D. Huffman, et al., "Functional Importance of Connective Tissue Repair During the Development OT Experimental Abdominal Aortic Aneurysms", Surgery, pp. 429-438, 2000.
Drazen Petrinec, et al., "Doxycycline Inhibition of Aneurysmal Degeneration in an Elastase-Induced Rat Model of Abdominal Aortic Aneurysm: Preservation of Aortic Elastin Associated With Suppressed Production of 92 kD Gelatinase", Journal of Vascular Surgery, vol. 23, No. 2, pp. 336-346, 1996.
Eric F. Steinmetz, et al., "Treatment With Simvastatin Suppresses the Development of Experimental Abdominal Aortic Aneurysms in Normal and Hypercholesterolemic Mice", Annals Surgery, vol. 241, No. 1, pp. 92-101, 2005.
Robert W Thompson, "Aneurysm Treatments Expand", Nature Medicine, vol. 11, No. 12, pp. 1279-1281, 2005.
Koutaro Tsunemi, et al., "A Specific Chymase Inhibitor, 2-(5-Formylamino-6-oxo-2-phenyl-1, 6-dihydropyrimidine-1-yl)-N-[{3,4-dioxo-1-phenyl-7-(2-pyridyloxy)}-2-heptyl] acetamide (NK3201), Suppresses Development of Abdominal Aortic Aneurysm in Hamsters", The Journal of Pharmacology and Experimental Therapeutics, vol. 309, No. 3, pp. 879-883, 2004.
Koichi Yoshimura, et al., "Regression of Abdominal Aortic Aneurysm by Inhibition of C-Jun N-Terminal Kinase", Nature Medicine, vol. 11, No. 12, pp. 1330-1338, 2005.
Yun Dai, et al., "Interruption of the NF-kB Pathway by Bay 11-7082 Promotes UCN-01-Mediated Mitochondrial Dysfunction and Apoptosis in Human Multiple Myeloma Cells", Blood, vol. 103, No. 7, pp. 2761-2770, 2004.

* cited by examiner

*Primary Examiner*—Ardin Marschel
*Assistant Examiner*—Gregg Polansky
(74) *Attorney, Agent, or Firm*—Oblon, Spivak, McClelland, Maier & Neustadt, L.L.P.

(57) ABSTRACT

The present invention relates to a prophylactic agent or a therapeutic agent for a disorder of collagen or elastin metabolism, which comprises a substance possessing JNK inhibitory activity as an active ingredient.

4 Claims, 9 Drawing Sheets

PREVENTIVE AND REMEDY FOR COLLAGEN OR ELASTIN METABOLIC DISORDER

TECHNICAL FIELD

The present invention relates to a prophylactic agent and a therapeutic agent for disorders of collagen or elastin metabolism, and particularly for aneurysms, and a method for screening for a substance possessing prophylactic activity or therapeutic activity against disorders of collagen or elastin metabolism.

BACKGROUND ART

Collagen and elastin are mainly distributed throughout skin, bones, cartilages, joints, and blood vessels. Furthermore, collagen and elastin are also broadly distributed throughout teeth, tendons, digestive tracts, lungs, uteri, and the like. Abnormalities in collagen or elastin metabolism are known to cause various disorders in all organs in which they are distributed. In particular, 40% of collagen is present in the skin and 20% is present in bones and cartilages. Collagen is also broadly distributed in blood vessels and visceral organs. As represented by a congenital disease, Ehlers-Danlos syndrome, it is well known that abnormalities in enzymes essential for collagen synthesis induce the development of symptoms including overelasticity and friability of the skin, hypermobility and dislocation of joints, fragility of the blood vessels and bleeding, or the like. Moreover, complications may be developed, for example, in cardiovascular system (e.g., heart valve disease, aortic dissection, and vascular bulge (aneurysm or varicose vein)), in osteocartilaginous system (e.g., osteoarthritis, deformity of spine, and hernia), in visceral system (e.g., bowel rupture, uterine rupture, bladder rupture, pneumothorax, and emphysema), in ophthalmic system (e.g., rupture of eyeballs and retinal detachment), and in dental system (e.g., loss of teeth and dental periostitis). An example of such a complication known for many years is scurvy, wherein abnormalities in collagen synthesis are caused by vitamin C deficiency. Scurvy causes fragile blood vessels, resulting in subcutaneous bleeding, gingival bleeding, or visceral bleeding as well as systemic symptoms such as fragile bones or skin.

Studies in recent years have revealed that collagen is required as a foothold upon bone or cartilage formation, thereby confirming the pathological conditions of osteocartilaginous symptoms due to abnormalities in collagen metabolism. Actually, clinical test results reported that the symptoms of osteoarthritis or chronic rheumatism are ameliorated by the administration of collagen or a collagen peptide. Furthermore, it has also been reported that in an animal experiment, osteoporosis was ameliorated by the administration of a collagen peptide. Collagen is also an essential factor in the healing of wounds. When collagen degradation levels are greater than collagen synthesis levels, the healing process does not work, and it may lead to ulceration.

Furthermore, collagen and elastin are distributed throughout the skin and are particularly distributed in dermis. They are thought to be essential for maintaining flexibility and elasticity of the skin, respectively. Abnormalities in collagen and elastin metabolism wherein degradation levels are higher than synthesis levels and total amounts of collagen and elastin decrease result in so-called skin-aging symptoms, such as wrinkles, sagging skin, and flecks. Skin-aging symptoms are increased by ultraviolet irradiation such as sunburn. However, it has been revealed in recent years that the pathogenesis thereof is also associated with abnormalities in collagen and elastin metabolism.

Furthermore, collagen and elastin are important in maintaining the strength and elasticity of the walls of blood vessels. In the cases of congenital diseases (e.g., Ehlers-Danlos syndrome) that are caused by abnormalities in the genes of enzymes required for the synthesis of collagen and elastin, it is known that aneurysm formation, the dissection of arteries, and arterial rupture occur. Similarly, it has been reported that aneurysm formation, the dissection of arteries, and arterial rupture are also developed in lysyl oxidase (LOX) gene-deficient mice (lacking LOX, which is an enzyme required for the synthesis of both collagen and elastin) and also in type I or type III collagen gene-altered mice. Moreover, it is thought that the onset of acute coronary syndrome (acute myocardial infarction, unstable angina, and sudden death) is due to the rupture of coronary atherosclerotic plaque. Enhanced collagen and elastin degradation and the resulting thinning and weakening of fibrous capsules are involved in the pathogenesis of unstable and easy-to-rupture plaques.

Various primary causes of aneurysms are known, such as arteriosclerosis, inflammation, infection, and congenital anomaly. All of these cases are characterized by dilatation of the aorta or the peripheral arteries. Specifically, such dilatation is due to weakening of aortic walls that is directly caused by abnormalities in collagen and elastin metabolism. As aneurysms, true aneurysms that involve dilation of all layers of the walls, and dissecting aneurysms that occur when blood flow forces the layers of the wall of the aorta apart are known. Both aneurysms are disorders that involve enlarged aneurysm diameter as the disorders progress and eventual rupture leading to death if untreated. Although aneurysms are clinically important disorders, currently the best available therapeutic method that can be employed for improving the prognosis is surgical therapy (e.g., surgical repair or stentgraft deployment) alone. However, surgery itself is severely burdensome for patients and surgical risk is often higher than the risk of aneurysmal rupture. Hence, a new low-invasive therapy for aneurysms, and particularly pharmacotherapy for the same, have been desired.

As described above, it is thought that aneurysms occur when the aortic wall is weakened due to enhanced degradation or abnormalities in the synthesis of the extracellular matrix, in particular, collagen and elastin that composes the aortic wall. Aneurysms then progress and result in rupture thereof. Actually, enhancement of various factors involving extracellular matrix degradation in human aortic aneurysms has been observed. In particular, matrix metalloproteases (MMPs) composing a group of extracellular-matrix-degrading enzymes, and are thought to be essential for the development and the progression of aneurysms and have been a focus of attention. Because the development of experimental aneurysms is prevented in mice lacking the genes of MMPs. Moreover, there is a report demonstrating prophylaxis with respect to the development of experimental aneurysms in model animals using a drug possessing MMP inhibitory activity. However, in the U.S. and Europe, clinical trials concerning MMP activity inhibitory agents have been conducted for preventing enlargement of aneurysm diameter in small-sized abdominal aortic aneurysms. Nevertheless, no significant effects of preventing the progress of aneurysms have been reported to date (J. Vascular Surgery 36: 1-12 (2002)).

DISCLOSURE OF THE INVENTION

Disorders due to abnormalities in collagen or elastin metabolism occur in various organs throughout the body, such as the skin, cardiovascular system, bones, cartilages, visceral organs, eyes, and teeth. The onset and the progress of aneurysms are directly caused by abnormal metabolism; that is, enhanced degradation and lowered or abnormal synthesis of collagen and elastin. Therefore, it is considered that these disorders can be ideally treated by ameliorating the direct causes thereof, that is, by ameliorating abnormalities in collagen or elastin metabolism. However, there have been no reports concerning any drug that possesses both activity to suppress collagen or elastin degradation and activity to enhance collagen or elastin synthesis, which would ameliorate abnormalities in collagen or elastin metabolism in an integrated way.

Aneurysm is a disease involving gradual progression when left untreated, followed by rupture leading to death. Aneurysms progress with almost no symptoms before rupture. In most actual cases, aneurysms have reached sizes such that there is a risk of rupture when they are discovered. The risk of rupture increases as aneurysm diameter increases. Accordingly, it is considered that "prevention of aneurysmal progression (to avoid further enlargement of the aneurysm)" can have sufficient therapeutic effects against small-sized aneurysms with almost no risk of aneurysmal rupture. However, it cannot be said that "prevention of aneurysmal progression" alone has therapeutic effects against large-sized aneurysms with the risk of aneurysmal rupture, because this cannot reduce the risk. Only when a method enables aneurysm regression and avoid the risk of aneurysmal rupture leading to death, such method can be said to constitute "effective and significant therapy." However, pharmacologic regression of aneurysms has been regarded as unrealistic. Furthermore, therapy that involves pharmacologic regression of aneurysms has never been reported, either conceptually or experimentally.

Hence, an object of the present invention is to provide a drug possessing both activity to suppress collagen or elastin degradation and activity to enhance collagen or elastin synthesis and ameliorating abnormalities in collagen or elastin metabolism. Another object of the present invention is to provide a prophylactic agent and a therapeutic agent for an aneurysm that is a type of disorder of collagen or elastin metabolism. More specifically, the object of the present invention is to provide a therapeutic agent and a prophylactic agent for aneurysms, which enables prevention of the development or progression of aneurysms or the inhibition of aneurysmal rupture through regression and repaircuring of aneurysms.

As a result of extensive searches for a JNK-dependent gene group by using a culture experimental system, the present inventors have discovered that: the expression of a gene group involved in degradation of the extracellular matrix components including collagen and elastin is enhanced in a JNK-dependent manner; and the expression of an enzyme group (prolyl 4-hydroxylase (P4H), lysyl hydroxylase (PLOD), and lysyl oxidase (LOX)) essential for collagen or elastin synthesis is lowered in a JNK-dependent manner. Based on these findings, the present inventors have studied the effects of JNK inhibitors on collagen or elastin metabolism in a culture experimental system. As a result, the present inventors have discovered that: substances possessing JNK inhibitory activity are effective as prophylactic and therapeutic agents for disorders of collagen or elastin metabolism; and the JNK inhibitors comprehensively correct the metabolism of collagen or elastin and promote the re-construction of the aneurysmal wall, thereby causing regression of aneurysms. Thus, the present inventors have completed the present invention The present invention encompasses the following inventions.

(1) A prophylactic agent or a therapeutic agent for a disorder of collagen or elastin metabolism, comprising as an active ingredient a substance possessing JNK inhibitory activity (2) The prophylactic agent or the therapeutic agent according to (1), wherein the disorder of collagen or elastin metabolism is at least one type selected from the group consisting of skin disorders, disorders of bones or cartilages, cardiovascular disorders, and disorders of visceral organs including lungs and digestive tracts.

(3) The prophylactic agent or the therapeutic agent according to (1) or (2), wherein the substance that possesses JNK inhibitory activity is a substance that restores the ability to synthesize collagen or elastin.

(4) The prophylactic agent or the therapeutic agent according to (3), wherein the substance that restores the ability to synthesize collagen or elastin is a substance that activates lysyl oxidase.

(5) The prophylactic agent or the therapeutic agent according to (3), wherein the substance that restores the ability to synthesize collagen or elastin is a substance that activates prolyl 4-hydroxylase.

(6) The prophylactic agent or the therapeutic agent according to (3), wherein the substance that restores the ability to synthesize collagen or elastin is a substance that activates lysyl hydroxylase.

(7) The prophylactic agent or the therapeutic agent according to any one of (1) to (6), wherein the disorder of collagen or elastin metabolism is an aneurysm.

(8) The prophylactic agent according to (7), wherein the substance that possesses JNK inhibitory activity is a substance that has a pharmacologic effect of suppressing aneurysmal progression.

(9) The therapeutic agent according to (7), wherein the substance that possesses JNK inhibitory activity is a substance that has a pharmacologic effect of causing the regression of an aneurysm.

(10) The prophylactic agent or the therapeutic agent according to any one of (7) to (9), wherein the aneurysm is an aortic aneurysm including a true aortic aneurysm and a dissecting aortic aneurysm.

(11) The prophylactic agent or the therapeutic agent according to any one of (7) to (9), wherein the aneurysm is an aortic aneurysm including including an abdominal aortic aneurysm and a thoracic aortic aneurysm.

(12) The prophylactic agent or the therapeutic agent according to any one of (1) to (11), wherein the substance that possesses JNK inhibitory activity is either a compound possessing JNK inhibitory activity or a pharmaceutically acceptable salt thereof.

(13) The prophylactic agent or the therapeutic agent according to (12), wherein the compound that possesses JNK inhibitory activity is pyrazoloanthrone or a derivative thereof.

(14) The prophylactic agent or the therapeutic agent according to any one of (1) to (11), wherein the substance that possesses JNK inhibitory activity is a peptide or a nucleic acid possessing JNK inhibitory activity.

(15) The prophylactic agent or the therapeutic agent according to (14), wherein the peptide that possesses JNK inhibitory activity is the D-stereoisomer of c-Jun N-terminal kinase peptide inhibitor 1 (D-JNKI1).

(16) The prophylactic agent or the therapeutic agent according to any one of (1) to (15), which is in the form of an injection.

(17) The prophylactic agent or the therapeutic agent according to any one of (1) to (15), which is in the form of an oral agent.

(18) The prophylactic agent or the therapeutic agent according to any one of (1) to (15), which is in the form of an external remedy.

(19) A method for screening for a substance possessing prophylactic activity or therapeutic activity against a disorder of collagen or elastin metabolism, which comprises determining the JNK inhibitory activity of a test substance.

(20) A method for screening for a substance possessing prophylactic activity or therapeutic activity against a disorder of collagen or elastin metabolism, which comprises determining both the activity of a test substance to suppress collagen or elastin degradation and the activity of the test substance to promote collagen or elastin synthesis.

Based on the finding of a pathogenesis mechanism whereby the activation of JNK results in both promoted collagen or elastin degradation and inhibited collagen or elastin regeneration at the same time, disorders of collagen or elastin metabolism, and particularly the development or progression of aneurysms can be prevented, or regression and repair of aneurysms can be achieved. Specifically, such prevention, regression, and repair can be achieved through integrated correction of these factors using JNK inhibitors—that is, prevention of collagen or elastin disruption—and aggressive restorement of tissue-reconstructing ability. According to the present invention, fundamental prevention of aneurysmal rupture can be achieved and the vital prognosis of aneurysm patients can be aggressively improved.

Figure 1:
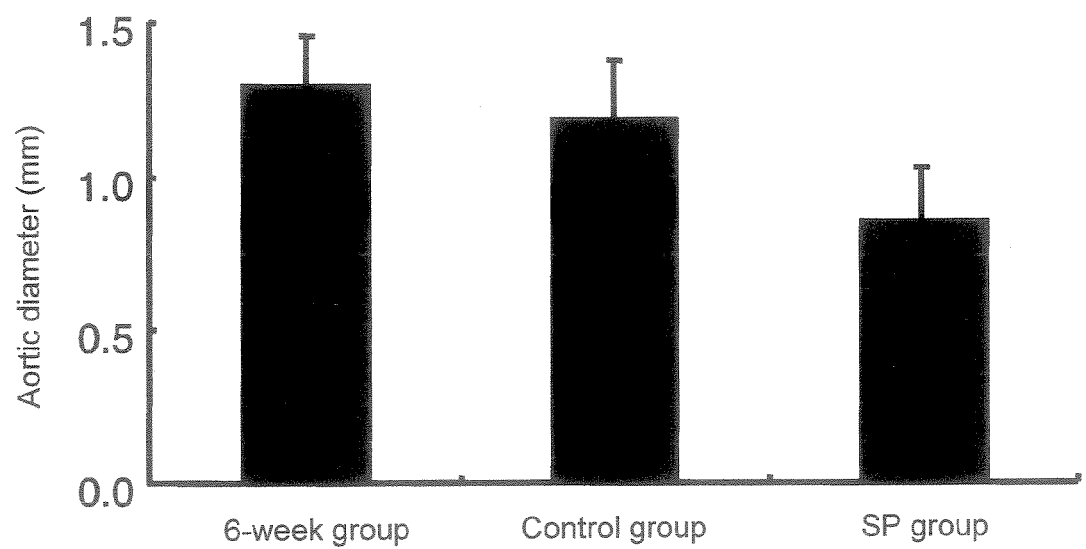
FIG. 1 is a graph showing the results of an experiment concerning aneurysm therapy and aneurysm regression in a calcium chloride-treated mouse aneurysm model through the use of a JNK inhibitor.

This description includes part or all of the contents as disclosed in the descriptions and/or drawings of Japanese Patent Application Nos. 2004-244316 and 2005-035769, which are priority documents of the present application.

BEST MODE FOR CARRYING OUT THE INVENTION

As a result of basic studies in view of the above technical background, the present inventors have discovered JNK as a key factor that integrally controls the metabolic balance of extracellular matrix components, including collagen and elastin resulting in enhancement of the degradation thereof, thus weakening the relevant tissues.

JNK is an enzyme that phosphorylates c-Jun at the amino-terminal region and is a type of MAP kinase. JNK is also a type of enzyme that is activated by a cytokine such as interleukin 1 (IL-1) or tumor necrosis factor-$\alpha$ (TNF-$\alpha$) or a physicochemical stress stimulus such as ultraviolet irradiation, heat shock, or hyperosmolarity. JNK is also known to phosphorylate AP-1 which is a transcription factor of a constitutive gene c-Jun and to induce the expression of a gene (e.g., Cox-2) involved in inflammation. JNK has also been thought to be involved in apoptosis. However, the role of JNK in the metabolic balance in the extracellular matrix and the role of JNK in disorders of collagen or elastin metabolism, and particularly in the pathogenesis of aneurysms, have remained unknown.

In the meantime, aneurysmal dilation is initiated when the aortic wall is weakened because of the enhanced degradation of extracellular matrix components, particularly, collagen or elastin, and cannot bear arterial pressure. Thus, it is concluded if such degradation system can be suppressed at the initial stage, aneurysms can be prevented from occurring. An actual report is already known that the development of experimental aneurysms is prevented through inhibition of factors of an extracellular matrix degradation system.

However, an aneurysm discovered in a clinical setting has an already enlarged aneurysm diameter and fragile aneurysmal walls. In such a case, even if the further degradation mechanism for the extracellular matrix is completely blocked, the affected wall will soon be unable to bear arterial pressure and thus rupture, unless the disrupted tissue construction is restored. Moreover, a wall with an enlarged diameter is subjected to pressure greater than that applied to an aortic wall with a normal diameter, as is known as Laplace's law. Therefore, to cause regression of a dilated aneurysm, it is essential to aggressively promote the regeneration of tissue construction through suppression of the enhancement of collagen or elastin degradation while restoring or enhancing the synthesis system thereof.

As a result of studies using culture experimental systems, the present inventors have discovered that activated JNK causes enhanced expression of a number of MMPs, lipocalin 2, inducible nitric oxide synthase (iNOS), IL-1, and the like, so that the activity of MMP-9, a major extracellular matrix-degrading enzyme, is significantly enhanced and tissue inhibitor of MMP (TIMP-3) is decreased. Furthermore, the present inventors have also discovered that in a number of culture experimental systems, JNK inhibitors not only inhibit MMP-9 activity, but also enhance the expression level and activity of lysyl oxidase and prolyl 4-hydroxylase, which are enzymes essential for collagen and elastin synthesis. Furthermore, the present inventors have focused on the fact that in a culture experimental system for human aneurysmal walls, JNK inhibitors integrally inhibit the activity of MMPs that degrade collagen or elastin. Thus, the present inventors have demonstrated that JNK inhibitors almost completely prevent mouse experimental aortic aneurysms from development. In addition, the present inventors have also succeeded in causing regression and repair of already developed mouse experimental aortic aneurysms through administration of JNK inhibitors, using the new discovery that substances possessing JNK inhibitory activity possess both activity to inhibit collagen or elastin degradation and activity to enhance collagen or elastin synthesis for our purpose. Pharmacologic regression and repair of existing aneurysms, which were previously totally conceptually unknown, have been achieved by the present inventors for the first time in the world.

It is generally thought that many proteases, including MMP, are involved in the disruption of tissue structure. In the case of aneurysms, Pyo et al's experiment has revealed that MMP-9 is particularly important (J. clin. Invest. 105:1641-1649 (2000)). Furthermore, Thompson et al's experimental results (J. clin. Invest. 96: 318-326 (1995)) obtained using clinical samples and McMillan et al's analytical results (Circulation 96: 2228-2232 (1997)) have revealed that MMP-9 enzymes are recognized at high levels also in human aneurysm tissues. In the meantime, abnormalities not only in degradation systems of extracellular matrix components (particularly collagen and elastin) but also in the synthesis systems thereof may be involved in the pathogenesis of aneurysms. According to O'Donnell et al, when such a synthesis system is suppressed through administration of a lysyl oxidase inhibitor to hyperlipidemia mice, aortic aneurysms occur (Circulation 108: (supplement IV), IV-252 (2003)). Moreover, when the present inventors transferred a lysyl oxidase gene into a mouse aneurysm model to restore the synthesis system, aortic aneurysmal progression was then suppressed.

In an embodiment of the present invention, the functions of factors (e.g., such as lipocalin 2, iNOS, IL-1, or MMP-9) that promote the disruption of extracellular matrix components composing tissues (in particular, aortic wall) are integrally inhibited through inhibition of JNK activity as described above; and the ability to synthesize extracellular matrix is restored by correction of the expression of procollagens (collagen precursors) and the expression of an enzyme group (lysyl hydroxylase, prolyl 4-hydroxylase, and lysyl oxidase) that is essential for extracellular matrix synthesis. As a result, tissue (in particular, aortic wall) construction is regenerated and a repair takes place.

Hence, in an embodiment of the present invention, inhibition of JNK activity directly improves the metabolic balances for the extracellular matrix components of tissues (in particular, aortic wall), and particularly collagen or elastin. This is effective for preventing or treating disorders of collagen or elastin metabolism, and in particular aneurysms. Pharmacologic means for inhibiting JNK are not particularly limited, as long as a substance that inhibits JNK activity effectively in vivo is used through administration by injection, oral administration, external administration, or the like.

JNKs in the present invention include JNK1, JNK2, and JNK3. It is known that some encoded isoforms are present with respect to 3 genes (JNK1, JNK2, and JNK3). Inhibition of JNK in the present invention includes both inhibition specific to these isoforms and inhibition not specific to the same.

Particularly concerning aneurysms, the present inventors have discovered that pharmacologic inhibition of JNK not specific to these isoforms exerts the effect of suppressing mouse aneurysm progression. However, an effect of suppressing aneurysms equivalent to the aforementioned effect is also exerted by specific inhibition of JNK2.

Disorders of collagen or elastin metabolism are of a disease group characterized by, as in the case of its typical example, Ehlers-Danlos syndrome, various symptoms following tissue weakening or disruption of tissue construction that are caused by abnormalities in collagen or elastin metabolism, such as overelasticity and friability of the skin, hypermobility and dislocation of joints, and fragility of blood vessels and bleeding. More specific examples of such disorders include disorders of the cardiovascular system (e.g., heart valve disease, aortic dissection, vascular aneurysm, and acute coronary syndrome), disorders of the osteocartilaginous system (e.g., osteoarthritis, deformity of spine, and hernia), disorders of the visceral system (e.g., bowel rupture, uterine rupture, bladder rupture, pneumothorax, and emphysema), disorders of the ophthalmic system (e.g., rupture of eyeballs and retinal detachment), disorders of the dental system (e.g., loss of tooth and dental periostitis), scurvy, which causes abnormalities in collagen synthesis due to vitamin C deficiency, and skin aging.

JNK inhibitors have an effect of ameliorating and normalizing pathologic collagen or elastin metabolism at the cellular and the tissue levels. Thus, the JNK inhibitors are thought to be reasonable prophylactic or therapeutic agents for the above disorders of collagen or elastin metabolism. The prophylactic agent or the therapeutic agent of the present invention is particularly suited to use in preventing or treating aneurysms.

Aneurysms in the present invention generally include all pathological conditions referred to as aneurysms.

Aneurysms are classified variously depending on their sites of development, causes, or shapes. Examples of aneurysms classified based on the sites of development include aortic aneurysms such as thoracic aortic aneurysms and abdominal aortic aneurysms, aneurysms of visceral organs such as cerebral aneurysms and renal aneurysms, and aneurysms that are formed in peripheral arteries. Based on the wall structure, aneurysms are classified into true aneurysms, dissecting aneurysms, pseudoaneurysms, and the like. Examples of aneurysms classified based on cause include arteriosclerotic aneurysms, inflammatory aneurysms, congenital aneurysms, and traumatic aneurysms or infectious aneurysms represented by bacterial aneurysms, mycotic aneurysms, syphilitic aneurysms, and the like. Examples of aneurysms classified based on shape include saccular aneurysms and fusiform aneurysms but are not particularly limited thereto in the present invention.

Prophylaxis (prevention) of aneurysms in the present invention includes not only "prevention of aneurysmal progression (to inhibit further enlargement of existing aneurysm diameter," but also prevention of the development of aneurysms through prevention of weakening of the walls of blood vessels. Prophylaxis of aneurysms in the present invention further includes prevention of rupture, which is achieved by the prevention of the development or progression of aneurysms. "Prevention of aneurysmal progression" alone can have an effect of preventing rupture, which is an object of aneurysm therapy, when the target is a small-sized aneurysm with almost no risk of aneurysmal rupture at the time of discovery. This has also significance, as in the case of "prevention of rupture." Hence, aneurysm therapy also includes prophylaxis in a broad sense. However, in the case of an existing aneurysm, "prevention of the development of aneurysms" has no therapeutic significance. Similarly, when an existing aneurysm is large enough to rupture, "prevention of aneurysmal progression" alone is insufficient for preventing its rupture and thus has low therapeutic significance. This is because the biggest challenge in treating aneurysms is to prevent bleeding to death due to aneurysmal rupture and to improve the prognosis of patients. Aneurysm therapy in the present invention encompasses fundamental aneurysm therapy, which involves causing the regression of an aneurysm already at risk of rupture or causing such aneurysm to disappear, so as to avoid the risk of rupture.

The present invention provides a prophylactic agent and a therapeutic agent for disorders of collagen or elastin metabolism (in particular, aneurysms), which possess both activity to suppress collagen or elastin degradation and activity to enhance collagen or elastin synthesis. At the same time, the present invention provides evaluation indices useful for selecting or identifying (screening for) a substance possessing prophylactic activity or therapeutic activity against disorders of collagen or elastin metabolism (in particular, aneurysms).

A first index concerns the ability to inhibit JNK activity. Specifically, in one embodiment, the present invention relates to a method for screening for a substance possessing prophylactic activity or therapeutic activity against disorders of collagen or elastin metabolism (and in particular, aneurysms), which comprises determining the JNK inhibitory activity of a test substance. More specifically, the JNK inhibitory activity of a test substance can be tested by cell-free kinase assay or the like, by which the effects of JNK1, JNK2, and JNK3 of suppressing the phosphorylation of a substrate c-Jun are detected. A test substance possessing JNK inhibitory activity can then be identified as a substance possessing prophylactic activity or therapeutic activity against disorders of collagen or elastin metabolism.

A second index concerns ability to suppress collagen or elastin degradation. Specifically, in one embodiment, the present invention relates to a method for screening for a substance possessing prophylactic activity or therapeutic activity against disorders of collagen or elastin metabolism (and in particular, aneurysms), which comprises determining the activity of a test substance to suppress collagen or elastin degradation. More specifically, the activity of a test substance to suppress collagen or elastin degradation can be determined by testing the suppression of the activity of MMP, which is a representative degrading enzyme for collagen or elastin, by an immunoassay method, a zymography method, or the like in a cultured cell system. A test substance possessing activity to suppress collagen or elastin degradation can be identified as a substance possessing prophylactic activity or therapeutic activity against disorders of collagen or elastin metabolism.

A third index concerns ability to promote collagen or elastin synthesis. Specifically, in one embodiment, the present invention relates to a method for screening for a substance possessing prophylactic activity or therapeutic activity against disorders of collagen or elastin metabolism (and in particular, aneurysms), which comprises determining the activity of a test substance to promote collagen or elastin synthesis. More specifically, the activity of a test substance to promote collagen or elastin synthesis can be determined by a method that involves detecting the effect of enhancing or restoring prolyl 4-hydroxylase (P4H), a lysyl hydroxylase (PLOD), and lysyl oxidase (LOX), which are essential synthases for collagen or elastin, in a cultured cell system for example, through assay using specific substrates at the activity level or through PCR at the expression level. A test substance possessing activity to promote collagen or elastin synthesis can be identified as a substance possessing prophylactic activity or therapeutic activity against disorders of collagen or elastin metabolism.

It is particularly effective to perform screening using indices relating to both ability to promote collagen or elastin synthesis and activity to suppress collagen or elastin degradation. Specifically, in one embodiment, the present invention relates to a method for screening for a substance possessing prophylactic activity or therapeutic activity against disorders of collagen or elastin metabolism (and in particular, aneurysms), which comprises determining both the ability of a test substance to promote collagen or elastin synthesis and the activity of the same to suppress collagen or elastin degradation.

With the use of these indices, a substance is selected in a step-by-step manner. As a result, a substance possessing prophylactic activity or therapeutic activity against disorders of collagen or elastin metabolism (and in particular, aneurysms) can be screened for. Examples of a test substance include, but are not particularly limited to, single compounds such as natural compounds, organic compounds, inorganic compounds, proteins, and peptides, compounds from compound libraries, expression products of gene libraries, cell extracts, cell culture supernatants, products of microorganism fermentation, marine-organism extracts, and plant extracts.

Examples of substances (which may also be referred to as "JNK inhibitors") possessing JNK inhibitory activity in the present invention include known compounds possessing JNK inhibitory activity (Nat. Rev. Drug. Discov. 2: 554-565 (2003); Curr. Drug. Targets. CNS Neurol. Disord. 1: 31-49 (2002); Trends Pharmacol. Sci. 23: 40-45 (2002); Circulation 109: 1196-1205 (2004); Curr. Opin. Pharmacol. 3: 420-425 (2003); Biochim. Biophys. Acta. 1697: 89-101 (2004); and Drug Discov. Today 9: 932-939 (2004)) or pharmaceutically acceptable salts thereof and known peptides or nucleic acids inhibiting JNK activity.

An example of a compound possessing JNK inhibitory activity described above is at least one compound selected from the group consisting of compounds represented by the following general formulae (1) to (13).

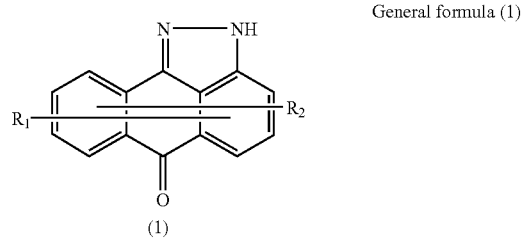

General formula (1)

(1)

[In the above formula, $R_1$ and $R_2$ may be the same or different and each represent a hydrogen atom, a halogen atom, or an alkyl, nitro, methyl trifluoride, sulfonyl, carboxyl, alkoxycarbonyl, alkoxy, aryl, aryloxy, arylalkyloxy, arylalkyl, cycloalkyl alkyloxy, cycloalkyloxy, alkoxyalkyl, alkoxyalkoxy, aminoalkoxy, or mono- or di-alkylamino alkoxy group, or any one group represented by the following formula (a), (b), (c), or (d).]

(a)

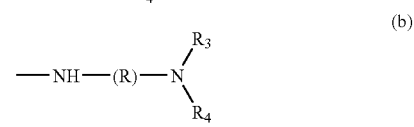

(b)

-continued

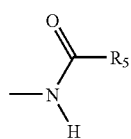
(c)

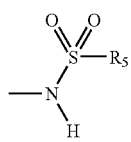
(d)

(The above R represents an alkylene group, $R_3$ and $R_4$ form an alkylene or hetero atom containing alkylene with connected ends, or may be the same or different and each represent a hydrogen atom or an alkyl, cycloalkyl, aryl, arylalkyl, cycloalkylalkyl, aryloxyalkyl, alkoxyalkyl, alkoxyamino, or alkoxy (mono- or di-alkylamino) group, and $R_5$ represents a hydrogen atom or an alkyl, cycloalkyl, aryl, arylalkyl, cycloalkylalkyl, alkoxy, amino, mono- or di-alkylamino, arylamino, arylalkylamino, cycloalkylamino, or cycloalkylalkylamino group.]

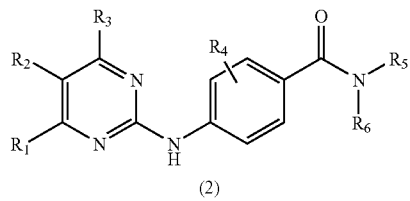

General formula (2)

(2)

[In the above formula, $R_1$ represents an unsubstituted or substituted aryl or heteroaryl group, $R_2$ and $R_3$ may be the same or different and each represent a hydrogen atom or a lower alkyl group, $R_4$ represents a hydrogen atom, a halogen atom, or a hydroxy, lower alkyl, or lower alkoxy group, and $R_5$ and $R_6$ may be the same or different and each represent a hydrogen atom or an alkyl, or unsubstituted or substituted aryl group.]

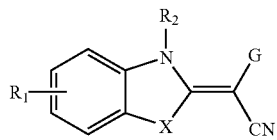

General formula (3)

(3)

[In the above formula, $R_1$ and $R_2$ each represent a hydrogen atom or a lower alkyl or lower alkoxy group, X represents O, S, or NH, and G represents an unsubstituted or substituted pyrimidinyl group.]

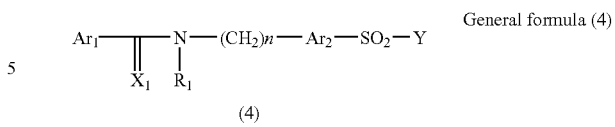

General formula (4)

(4)

[In the above formula, $Ar_1$ and $Ar_2$ independently of one another represent an unsubstituted or substituted aryl or heteroaryl group, $R_1$ represents a hydrogen atom or a lower alkyl group, n represents an integer between 0 and 5, $X_1$ represents O or S, and Y represents an unsubstituted or substituted 4- to 8-membered hetero ring containing at least one hetero atom or an unsubstituted or substituted aryl or heteroaryl group.]

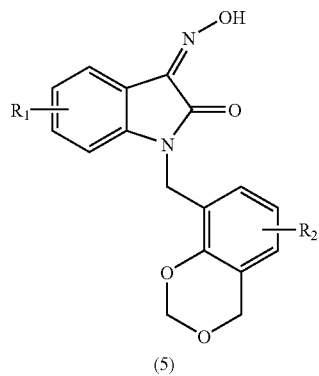

General formula (5)

(5)

[In the above formula, $R_1$ and $R_2$ independently of one another represent a hydrogen atom, a halogen atom, or a hydroxy, lower alkyl, or lower alkoxy group.]

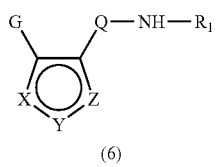

General formula (6)

(6)

[In the above formula, X-Y-Z is selected from any one of the following formulae:

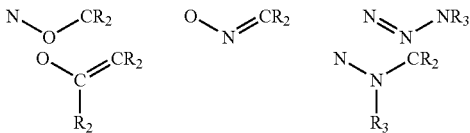

$R_1$, $R_2$, and $R_3$ independently of one another represent a hydrogen atom or a lower alkyl, cycloalkyl, unsubstituted or substituted aryl, or arylalkyl group, G represents an unsubstituted or substituted aryl or heteroaryl group, and Q-NH is represented by the following formula:

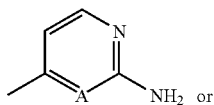 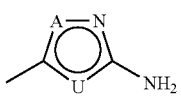

(In the above formulae, A represents N and U represents O, S, or NH)]

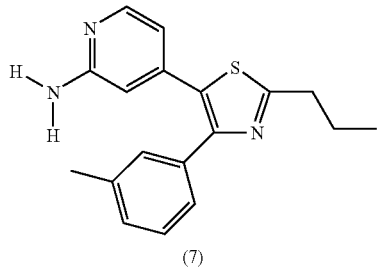

Formula (7)

(7)

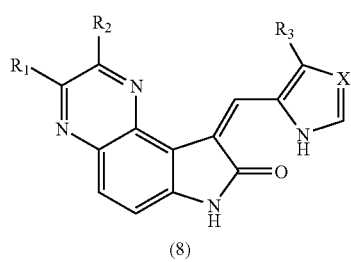

General formula (8)

(8)

[In the above formula, $R_1$, $R_2$, and $R_3$ independently of one another represent a hydrogen atom, a halogen atom, or a hydroxy, lower alkyl, lower alkoxy, unsubstituted or substituted aryl, or heteroaryl group and X represents N or CH.]

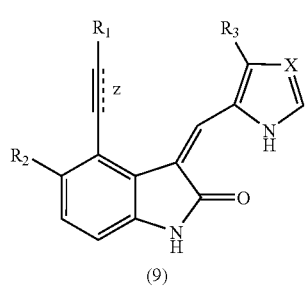

General formula (9)

(9)

[In the above formula: $R_1$ represents an unsubstituted or substituted aryl, aryloxy, heteroaryl, heteroaryloxy, or lower alkyl group substituted with a substituted heteroaryloxy group; $R_2$ and $R_3$ each represent a hydrogen atom, a halogen atom, or a hydroxy lower alkyl, lower alkoxy, unsubstituted or substituted aryl, or heteroaryl group; and X represents N or CH; and a bond shown with a dotted line "z" may be formed arbitrarily.]

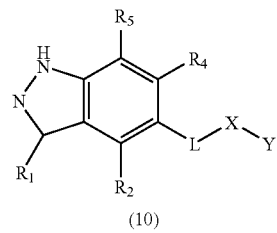

General formula (10)

(10)

[In the above formula, $R_1$, $R_2$, $R_4$, and $R_5$ independently represent a hydrogen atom, a halogen atom, or a hydroxy, lower alkyl, lower alkoxy, unsubstituted or substituted aryl, or heteroaryl group, L-X-Y represents NH—CO—R, and R represents an unsubstituted or substituted arylalkyl or heteroarylalkyl group.]

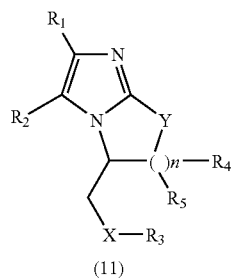

General formula (11)

(11)

[In the above formula: $R_1$, $R_2$, $R_4$, and $R_5$ independently of one another represent a hydrogen atom, a halogen atom, or a hydroxy, lower alkyl, lower alkoxy, unsubstituted or substituted aryl, or heteroaryl group; $R_3$ forms together with X a completely saturated 5- to 7-membered ring, wherein each saturated carbon in the ring is further arbitrarily and independently substituted with =O or =S; Y represents CH or N; and n represents 1.]

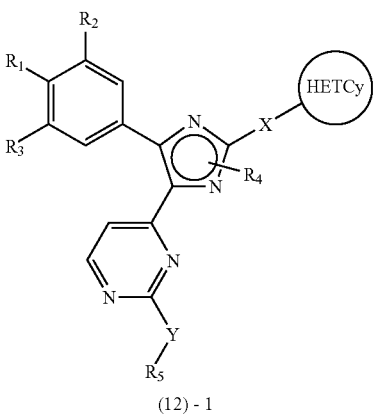

General formula (12)

(12) - 1

-continued

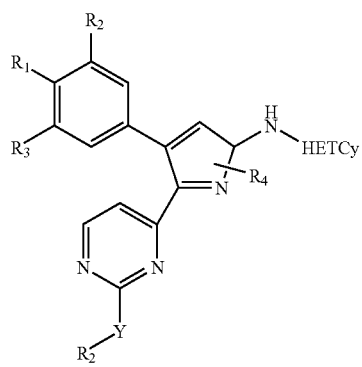

(12)-2

[In the above formula, $R_1$, $R_2$, $R_3$, $R_4$, and $R_5$ independently of one another represent a hydrogen atom, a halogen atom, or a hydroxy, lower alkyl, lower alkoxy, unsubstituted or substituted aryl, cycloalkane, or heteroaryl group, X represents a bond or an alkyl bridge having 1 to 3 carbons or forms together with HETCy a completely saturated 5- to 7-membered ring, Y represents —NH, and HETCy represents a 4- to 6-membered heteroaryl group containing at least one N atom.]

General formula (13)

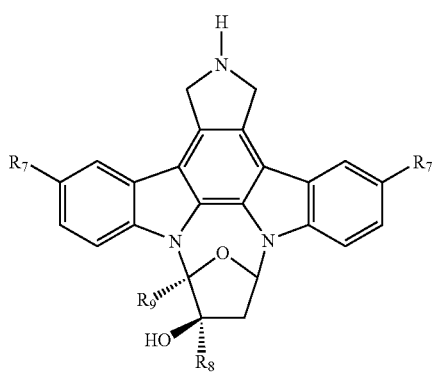

13

[In the above formula, $R_7$ represents an alkylenethioalkyl or alkylenealkylether group and $R_8$ and $R_9$ each independently represent a hydrogen atom, a halogen atom, or a hydroxy, lower alkyl, lower alkoxy, or alkoxyalkyl group.]

Among the compounds exemplified and represented by the above formulae, specific examples of compounds that can be particularly effective JNK inhibitors are represented by the following formulae (1) to (13) numbered with numbers corresponding to the above compounds.

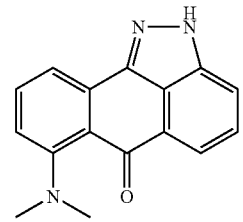
(1)

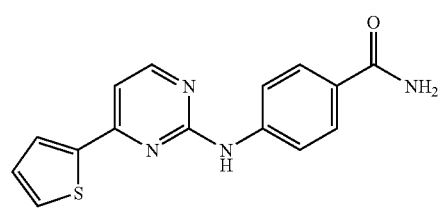
(2)

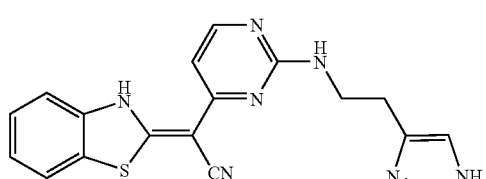
(3)

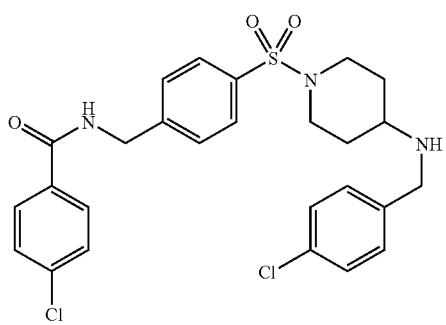
(4)

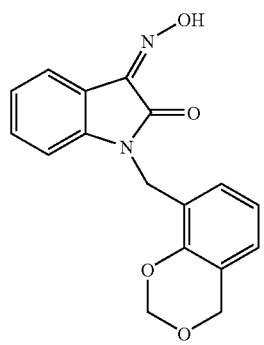
(5)

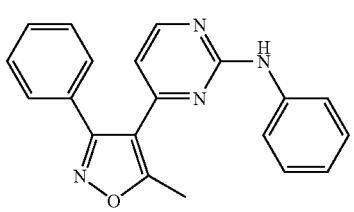
(6)

-continued (7)
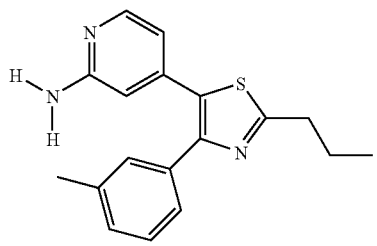

(8)
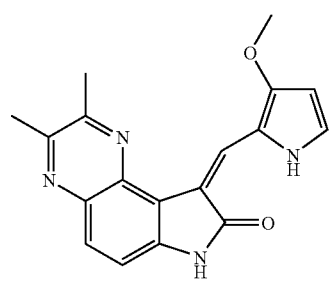

(9)
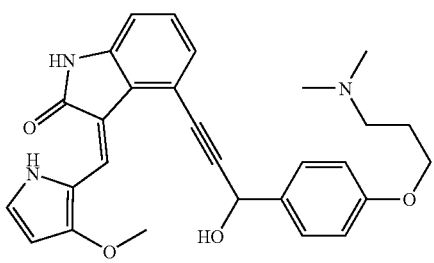

(10)
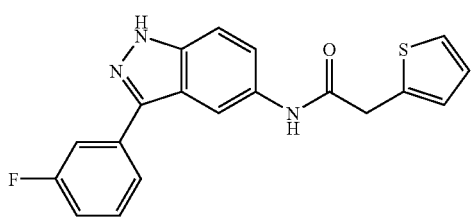

(11)
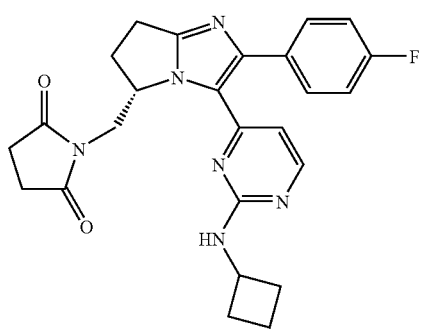

-continued

(12)
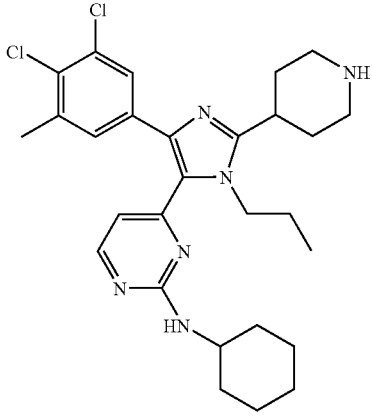

(13)

Among these compounds, a compound represented by general formula (1) has particularly good effects and is particularly desirably formulated into an injection as a prophylactic agent or a therapeutic agent. An anilino pyrimidine derivative represented by the above formula (2) can also be used as an injection and can be particularly effectively used as an oral agent. Hence, such derivative can naturally be used for therapy, and the excellent usefulness thereof as a prophylactic agent can be expected in the present invention. Compounds represented by the above formulae (3) and (4) are particularly effective as oral agents.

Anthra[1-9-cd]pyrazol-6(2H)-one (Anthrapyrazol-6-one) having a pyrazoloanthrone skeleton, which is represented by formula (1), is commercially available as the product with the name of SP600125. With its competitive inhibitory effect on ATP, the compound is used for suppressing AP-1 transcriptional activity in cells stimulated by IL-1, inhibiting the expression of the inflammatory genes (Cox-2, IL-2, IFN-γ, and TNF-α) in human peripheral blood monocytes, suppressing MMP expression and bone disruption in arthritis model animals, or suppressing TNF-α expression that is induced by LPS so as to suppress apoptosls.

Compounds that are used in the present invention may also be pharmaceutically acceptable salts. In the cases of basic compounds, examples of such salts include salts formed with an organic acid (e.g., carboxylic acid and sulfonic acid), sulfuric acid, hydrochloric acid, mineral acid, or the like. In the case of acidic compounds, examples of such salts include salts formed with an alkali metal, an alkaline-earth metal, an organic base, or the like. Examples of such organic acid (e.g., carboxylic acid and sulfonic acid) include acetic acid, adipic acid, benzoic acid, citric acid, fumaric acid, aspartic acid, lactic acid, malic acid, palmitic acid, salicylic acid, tartaric acid, benzenesulfonic acid, camphasulfonic acid, and toluenesulfonic acid. Examples of such mineral acid include hydrochloric acid, hydrobromic acid, sulfuric acid, and phosphoric acid. Examples of such alkali metal, alkaline-earth metal, organic base, and the like include lithium, sodium, potassium, calcium, magnesium, barium, tetramethylammonium, and tetrabutylammonium.

Compounds that are used in the present invention encompass optically active substances, racemic bodies, diastereoisomers, or mixtures of diastereoisomers, and all enatiomers including individual enantiomers and mixtures of enantiomers. Furthermore, regarding the binding positions of substituents and the like, all positional isomers that can bind are included herein, unless particularly limited. Moreover, various polymorphisms such as solvates (e.g., hydrates) and tautomers of solvates are also included in the compounds that are used in the present invention.

The series of compounds represented by the above general formulae in the present invention are all produced by production methods disclosed in JP Patent Publications (Kokai koho) and International Patent Publications (Kokusai Kohyo Koho) that are cited herein. However, the methods for producing such compounds are not limited to these methods.

When the group (series) of compounds represented by the above general formulae are used in the present invention as substances possessing JNK inhibitory activity, each compound is used alone or formulated into a preparation (e.g., an injection, a tablet, a granule, a subtle granule, a powder, a capsule, an adhesive preparation, an ointment, a spray, a solution, or a sustained release preparation) through mixture with a solubilizing agent, an extending agent, an excipient, or a carrier. As an additive such as an excipient, a carrier, or the like, a pharmaceutically acceptable one is selected. Types and compositions of such additives are selected depending on the route or the method of administration. For example, in the case of injections, common salt and saccharides such as glucose and mannitol are generally desired. In the case of oral agents, starch, lactose, crystalline cellulose, magnesium stearate, and the like are desired.

Examples of routes of administration include oral administration, administration by injection, or parenteral systemic administration using an external remedy or the like. In addition, direct topical administration to a lesion or a site in the vicinity of a lesion using an ointment, a solution, an adhesive preparation, a spray, or the like and remote administration to a lesion or a site in the vicinity of a lesion using a catheter or the like may be employed. In the case of an aneurysm prophylactic agent, oral administration is particularly preferable. In the case of an aneurysm therapeutic agent, not only an oral agent, but also an injection, a drug-combined stentgraft, and the like are also desirable, depending on the degree of the risk of rupture. More specifically, a stent, a graft, or an integrated form thereof (a stentgraft), is combined with a drug, and the resultant is placed in a vascular lesion or in a site in the vicinity of a lesion, so as to achieve sustained release of the drug, for example. Good results are expected from current less-invasive intravascular therapy using a stentgraft when the shape of the stentgraft agrees with the anatomic findings concerning an aneurysm. When a stentgraft does not agree with the same, no therapeutic effects can be expected. Successful agreement is currently limited depending on anatomic findings concerning a given aneurysm. The aneurysm prophylactic agent of the present invention can ameliorate anatomic abnormal findings concerning an aneurysm with its effect of causing aneurysmal regression. Hence, it can be expected that stentgraft therapy combined with an aneurysm therapeutic agent will be applied to a greater number of aneurysm patients. Furthermore, desirable forms of therapeutic agents for disorders of collagen or elastin metabolism in the skin, bones, cartilages, or joints include not only oral agents and injections, but also external remedies such as adhesive preparations, ointments, and sprays.

The content of the above compound in the prophylactic agent or the therapeutic agent of the present invention is varied depending on the preparation thereof. It generally ranges from 0.001% to 100% by weight and preferably ranges from 0.01 % to 98% by weight. For example, in the case of an injection, the active ingredient is generally 0.001% to 30% by weight and preferably 0.01% to 10% by weight. In the case of an oral agent, it is used together with an additive, in the form of a tablet, a capsule, a powder, a granule, a solution, a dry syrup, or the like. In such a capsule, tablet, granule, or powder, the active ingredient is generally 0.1% to 100% by weight and preferably 1% to 98% by weight. The dose is determined depending on a patient's age, body weight, symptoms, and the like. The dose generally ranges from 0.001 to 10 mg/kg/day in the case of parenteral administration and ranges from 0.01 to 100 mg/kg/day in the case of oral administration. When each compound is used in the form of a solution, a solution with a concentration between 1 nM and 1000 nM is used.

In the present invention, when a prophylactic agent or a therapeutic agent for aneurysms that contains a JNK inhibitor as an active ingredient is formulated into an injection, such agent may be used in the form of a solution that is harmless to the human body. According to a preferred embodiment, such solution can be an emulsion solution of 30% polyethylene glycol (molecular weight between approximately 300 and 500), 20% propylene glycol, 15% Cremophol EL, 5% ethanol, and 30% physiological saline.

Moreover, in the present invention, peptides, nucleic acids, or the like that inhibit JNK activity can be used as JNK inhibitors.

Specifically, examples of such peptides and nucleic acids include the following: (i) JNK inhibitor peptides and derivatives, fragments, analogs, and homologs thereof, either singly or in combination; (ii) nucleic acids encoding JNK inhibitor peptides or derivatives, fragments, analogs, or homologs thereof; (iii) all antibodies against JNK, fragments containing antigen recognition sites, or nucleic acids encoding the same; (iv) the antisense nucleic acid or the interfering RNA for the sequence encoding JNK and nucleic acids encoding them; and (v) modulators (that is, inhibitors, agonists, and antagonists).

Specific examples of the above peptides or nucleic acids that inhibit JNK activity include c-Jun N-terminal Kinase Peptide Inhibitor 1, L-stereoisomer (L-JNKI 1, ALEXIS, Nat. Med. 9: 1180-1186 (2003)), c-Jun N-terminal Kinase Peptide Inhibitor 1, D-stereoisomer (D-JNKI 1, ALEXIS, Nat. Med. 9: 1180-1186 (2003)), JNK antisense oligonucleotide (J. Biol. Chem. 272: 33422-33429 (1997)), JNK interfering RNA (J. Biol. Chem. 279: 40112-40121 (2004)), dominant negative JNK (J. Biol. Chem. 274: 32580-32587 (1999)), and JNK interacting protein-1 (JIP-1, Science. 277: 693-696 (1997)).

The JNK inhibitors, peptides, fusion peptides, and nucleic acids of the present invention can be formulated into pharmaceutical compositions. Each such composition can contain a pharmaceutically acceptable excipient, carrier, buffering agent, stabilizing agent, or other materials known to persons skilled in the art, in addition to one of the above substances. Such materials should be nontoxic and should not interfere with the effects of the active ingredient. The precise characteristics of carriers or other materials can depend on the route of administration (e.g., oral, intravenous, percutaneous, subcutaneous, transnasal, intramuscular, and intraperitoneal administration).

Pharmaceutical compositions for oral administration can be in the form of tablets, capsules, powders, or liquids. Such a tablet can contain a solid carrier (e.g., gelatin or adjuvant). Such a liquid pharmaceutical composition generally contains a liquid carrier (e.g., water, animal oil, plant oil, or synthetic oil). A physiological saline solution, dextrose or another sugar solution, or glycol (e.g., ethylene glycol, propylene glycol, or polyethylene glycol) can also be contained.

For intravenous injection, percutaneous or subcutaneous injection, or injection into affected sites, an active ingredient is in the form of a parenterally acceptable aqueous solution or an emulsion solution which contains no pyrogens but possesses appropriate pH, isotonicity, and stability. Persons in the related fields can prepare an appropriate solution using an isotonic vehicle (e.g., a physiologic saline injection, Ringer's injection, and lactate Ringer's injection), for example. A preservative, a stabiizing agent, a buffering agent, an antioxidant and/or other additives can also be contained, if necessary.

In the present invention, the use of a drug containing a substance possessing JNK inhibitory activity as an active ingredient makes it possible to prevent or treat disorders of collagen or elastin metabolism (and in particular, aneurysms). Such drug may be in the form of a composition prepared by combining a substance possessing JNK inhibitory activity with a pharmaceutically acceptable carrier, diluent, or excipient or in the form of a composition further containing various other agents. Embodiments concerning the use of such composition are not important and the means for incorporating such drug, such as injection or oral administration are not particularly limited.

Examples using an anthra[1-9-cd]pyrazol-6(2H)-one compound (SP600125 (Tocris Bioscience: pyrazoleanthrone)) having a pyrazoloanthrone skeleton, represented by the above formula (1) are given below.

EXAMPLES

Example 1

JNK Inhibition Experiment Using a Calcium Chloride-Treated Mouse Aneurysm Model

Methods

An abdominal aortic aneurysm model was generated by treating mice with calcium chloride according to Longo et al's method (J. Clin. Invest. 110: 625-632 (2002)). Specifically, the abdominal cavity of each 7-week-old male C57BL/6 mouse was opened, the infrarenal abdominal aorta was treated with cotton impregnated with 0.5 M calcium chloride for 15 minutes, and then the abdominal cavity was closed. Aneurysms that gradually become dilated by week 10 are formed by this treatment. A sham surgery group was treated with physiological saline. A JNK inhibitor SP600125 (Tocris Bioscience: pyrazoleanthrone) (SP group) or a solution (control group) alone was subcutaneously injected daily into mice treated with calcium chloride. SP600125 was adjusted when used to a final concentration of 4.2 mg/ml according to Bennett et al's method (Proc. Natl. Acad. Sci. U.S.A. 98: 13681-13686 (2001)) with a solution (30% polyethylene glycol-400, 20% polypropylene glycol, 15% Cremophol EL, 5% ethanol, and 30% physiological saline). The thus adjusted SP600125 was subcutaneously injected daily (twice a day) at a dose of 60 mg/kg/day. Following 10 weeks of postoperative rearing, the mice were sacrificed. The maximum diameter of the infrarenal abdominal aorta was measured. Furthermore, each aorta was excised and then subjected to histological analysis.

Results

Aortic diameters measured on week 10 after operation were: 0.68 mm±0.12 mm in the sham surgery group (8 mice); 1.10 mm±0.24 mm in the control group (9 mice); and 0.74 mm±0.16 mm in the SP group (8 mice). Aortic diameters in the control group treated with calcium chloride were significantly increased compared with those of the sham surgery group, indicating aneurysm formation in the control group. Aortic diameters in the SP group to which SP600125, a JNK inhibitor, had been administered daily were significantly smaller compared with those in the control group to which none had been administered. Furthermore, aortic diameters in the SP group were equivalent to those in the sham surgery group. It was indicated that aneurysm formation had been significantly suppressed in the SP group (Fisher's exact test: $p<0.01$). In the aortic walls of the control group treated with calcium chloride, findings characteristic of human abdominal aneurysms such as medial thinning and disrupted elastic fibers were histologically observed. In contrast, in the SP group, the wall structures were well maintained to a degree equivalent to those in the sham surgery group, and aneurysm formation was inhibited histologically.

Example 2

JNK Inhibition Experiment Using an apoE Knockout Mouse Aneurysm Model

Methods

An abdominal aortic aneurysm model was generated through continuous administration of angiotensin II to apolipoprotein E (apo E) knockout mice according to Daugherty et al's method (J. Clin. Invest. 105: 1605-1612 (2000)). Specifically, mini-osmotic pump (Alzet) was implanted into 24-week-old apoE knockout male mice and angiotensin II (1 µg/min/kg) was continuously infused. These model mice were affected with hyperlipidemia, hypertension, and marked aortic arteriosclerosis. As a result of 4 weeks of angiotensin II infusion, aneurysm formation was observed mainly in the suprarenal abdominal aorta of these mice. Some of these mice died due to aneurysmal rupture. The model exhibited disease conditions that extremely resemble those of clinically observed human aneurysms. Simultaneously with the initiation of continuous infusion of angiotensin II, daily subcutaneous injection of a JNK inhibitor SP600125 (SP group: 8 mice) or a solution (control group: 16 mice) without JNK inhibitor was initiated. The method employed herein for administration of SP600125 was similar to that in Example 1 above. On week 4, the maximum diameter of each abdominal aorta was measured using ultrasonic diagnostic equipment.

Results

Aortic diameters measured on week 4 after angiotensin II infusion were: 1.55 mm±0.19 mm in the control group; and 1.29 mm±0.18 mm in the SP group. Aortic diameters in the SP group to which the JNK inhibitor SP600125 had been administered daily were smaller than those in the control group to which none had been administered, indicating significantly suppressed aneurysm formation (t-test: $p<0.05$). Furthermore, some of these mice died due to the onset of abdominal aortic aneurysmal rupture or dissecting aortic aneurysm by week 5 after the initiation of angiotensin II infusion. Cumulative survival rate of the control group was 6.25%, whereas the same of the SP group was 87.5%. Survival rate of the SP group was higher than that in the control group.

Example 3

Experiment Concerning Aneurysm Therapy and Aneurysm Regression Using a JNK Inhibitor in Calcium Chloride-Treated Mouse Aneurysm Model Methods An abdominal aortic aneurysm model was generated by treating mice with calcium chloride according to Longo et al's method (J. Clin. Invest. 110: 625-632 (2002)). Specifically, the abdominal cavity of each 7-week-old male C-57BL/6 mouse was opened, the infrarenal abdominal aorta was treated with cotton impregnated with 0.5 M calcium chloride for 15 minutes, and then the abdominal cavity was closed. Following 6 weeks of rearing after treatment with calcium, the mice were divided randomly into 3 groups. Mice of a 6-week group were sacrificed on week 6 after treatment with calcium and then the maximum diameter of the abdominal aorta was measured. On week 6 after treatment with calcium, daily subcutaneous injection of a JNK inhibitor SP600125 (SP group) or a solution alone (control group) to the mice of the other 2 groups was initiated. The method employed herein for administration of SP600125 and the solution was similar to that in Example 1 above. Mice of the SP group and the control group were sacrificed on week 12 after treatment with calcium (week 6 after the initiation of injection) and then the maximum diameter of the abdominal aorta was measured.

Results

The maximum abdominal aortic diameters in the 6-week group (9 mice) were 1.29 mm±0.16 mm. Thus, the formation of aneurysms with diameters each enlarged to about twice the normal diameter was confirmed. The maximum aortic diameters in the control group (9 mice) and in the SP group (9 mice) were 1.18 mm±0.19 mm and 0.85 mm±0.18 mm, respectively. Aortic diameters in the SP group were significantly smaller than those in the control group (t-test: $p<0.01$) (see FIG. 1).

Accordingly, the therapeutic effect of the JNK inhibitor SP600125 was demonstrated when administration had been performed after aneurysm formation. Furthermore, aortic diameters in the SP group were significantly smaller than those in the 6-week group (t-test: $p<0.01$). Therefore, the effect of the JNK inhibitor SP600125 of causing aneurysm regression was demonstrated in the calcium-treated aneurysm model.

Example 4

Experiment Concerning Aneurysm Therapy and Aneurysm Regression Using a JNK Inhibitor in an apoE Knockout Mouse Aneurysm Model Methods An abdominal aortic aneurysm model was generated through continuous administration of angiotensin II to apoE knockout mice according to Daugherty et al's method (J. Clin. Invest. 105: 1605-1612 (2000)). Specifically, mini-osmotic pump (Alzet) was implanted into 24-week-old apoE knockout male mice and angiotensin II (1 µg/min/kg) was continuously infused. These model mice were affected with hyperlipidemia, hypertension, and marked aortic arteriosclerosis. Angiotensin II infusion resulted in aneurysm formation in the abdominal aorta. Some of these mice died due to aneurysmal rupture. The model exhibited disease conditions that extremely resemble those of clinically observed human aneurysms. After completion of 4 weeks of angiotensin II infusion, the lumen diameter of each abdominal aortic aneurysm was measured using ultrasonic diagnostic equipment. The mice were evenly divided into 2 groups based on the measured values. Immediately after grouping, daily subcutaneous injection of the JNK inhibitor SP600125 (SP group) or a solution alone (control group) was initiated. The method employed herein for administration of SP600125 and the solution was similar to that in Example 1 above. On week 8 after the initiation of injection, the aneurysm diameter of each abdominal aortic aneurysm was measured again using ultrasonic diagnostic equipment.

Results

Figure 2:
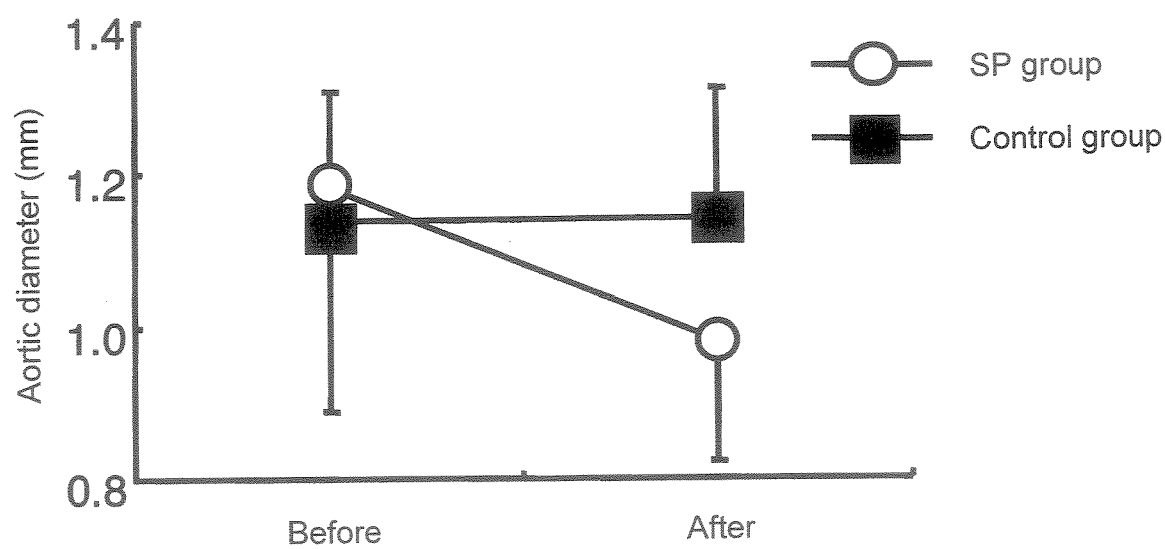
FIG. 2 is a graph showing the results of an experiment concerning aneurysm therapy and aneurysm regression in an apoE knockout mouse aneurysm model through the use of a JNK inhibitor.

After completion of angiotensin II infusion, aortic aneurysm diameters measured before the initiation of injection were: 1.14 mm±0.17 mm in the control group (5 mice); and 1.18 mm±0.16 mm in the SP group. Almost equal-sized aneurysms existed in the 2 groups. Aneuerysm diameters following 8 weeks of injection were 0.98 mm±0.16 mm in the SP group (6 mice) to which the JNK inhibitor SP600125 had been administered daily. This figure was significantly reduced compared with that before the initiation of injection (t-test: $p<0.05$). Reduction percentages obtained based on comparison of the value before injection and the value after injection were: 17% ±10% in the SP group; but 0%±13% in the control group. Thus, a significant difference between the 2 groups was confirmed (t-test: $p<0.05$) (see FIG. 2).

Based on the above results, the effects of the JNK inhibitor SP600125 of treating aneurysms and causing aneurysm regression in the apoE knockout mouse aneurysm model that is more human-aneurysm-like.

Example 5

Effect of a JNK Inhibitor Peptide in Cultured Cells

Methods

To verify the effects of a JNK inhibitor peptide, an experiment was conducted using MMP-9 as an index, which is thought to be important in the pathogenesis of aneurysms, in a cultured cell system. Cells used herein were macrophage cells (THP-1) mainly expressing MMP-9 in human aneurysms. Specifically, a JNK inhibitor peptide D-JNKI1 (ALEXIS) was administered at various concentrations (0, 1, 2, and 5 µM D-JNKI1) in advance to cultured THP-1 cells. D-TAT (ALEXIS) was used as a control peptide. At 24 hours after peptide administration, the cells were stimulated with TNF-α (50 ng/ml), an inflammatory cytokine. 48 hours later, culture solutions were collected and then the amounts of MMP-9 secreted in the culture solutions were subjected to quantitative analysis by the gelatin zymography method.

Results

Figure 3:
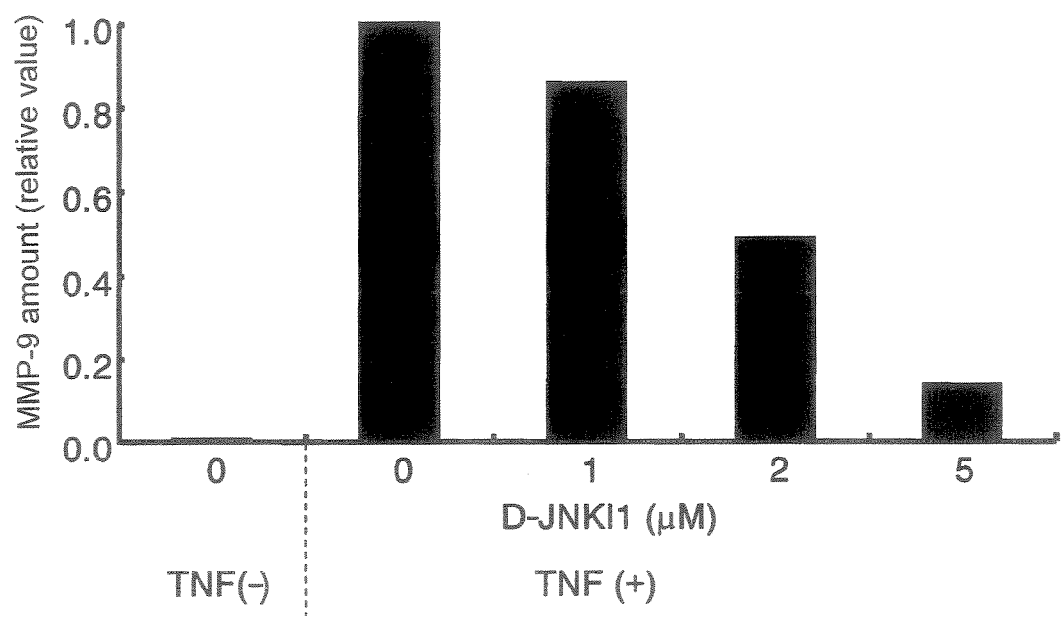
FIG. 3 is a graph showing the effect of a JNK inhibitor peptide of suppressing MMP-9 (an enzyme degrading collagen or elastin) in cultured cells.

Cultured THP-1 cells showed significant MMP-9 secretion due to stimulation with TNF-α. D-JNKI1 suppressed MMP-9 secretion due to TNF-α in a concentration-dependent manner The effect of suppressing MMP-9 was not confirmed in the control peptide D-TAT with the same concentration as that of D-JNKI1. These results showed that the JNK inhibitor peptide D-JNKI1 has the effect of suppressing collagen or elastin degradation (see FIG. 3).

Example 6

Effect of a JNK Inhibitor Peptide in a Human Aneurysmal Wall Culture System Methods Aneurysmal wall tissue excised at the time of operation of human abdominal aortic aneurysms was chopped and then cultured. The ability of aneurysmal wall to newly synthesize collagen was analyzed using 3H-labeled proline that is abundantly contained in collagen according to the Kidwell et al's method (Methods in Enzymology 147: 407-414 (1987)). Specifically, 3H-labeled proline (3 µCi/ml) was added to media to initiate culture. Immediately after culture initiation, a JNK inhibitor peptide (D-JNKI1, 5 mM, ALEXIS) was administered. D-TAT (5 mM, ALEXIS) was used as a control peptide. At 12 hours after peptide administration, stimulation was performed with TNF-α (R&D Systems, 100 ng/ml). TNF-α is an inflammatory cytokine that is increased in human aortic aneurysms and is known to activate JNK. 48 hours later, proteins in the culture supernatants were collected. 3H-labeled proline that had been incorporated for novel synthesis was measured using a scintillation counter.

Results

Figure 4:
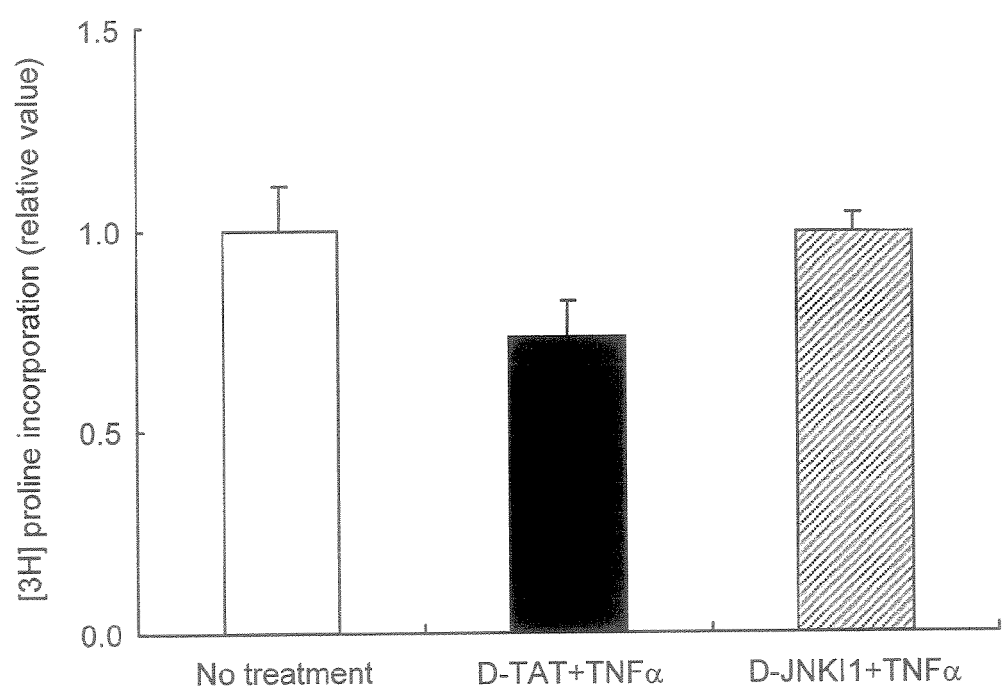
FIG. 4 is a graph showing the effect of a JNK inhibitor peptide of promoting the restorement of ability to synthesize collagen in a human aneurysmal wall culture system.

Incorporation of 3H-labeled proline was decreased in the cultured aneurysmal tissue due to stimulation with TNF-α. This means that novel collagen synthesis was suppressed by inflammatory stimulation. D-JNKI1 significantly restored 3H-labeled proline incorporation that had been decreased by TNF-α ($p<0.05$). Specifically, it was demonstrated that D-JNKI1 has the effect of restoring, with its JNK inhibitory activity, the ability of human aneurysmal wall to synthesize collagen (see FIG. 4).

Example 7

Effect of a JNK Inhibitor Peptide on Ability to Synthesize Collagen

Methods

An experiment was conducted using a vascular smooth muscle cell primary culture system isolated from a rat aorta. Among newly-synthesized proteins into which 3H-labeled proline had been incorporated, fractions that are specifically degraded by collagen degrading enzymes were subjected to quantitative analysis according to Kidwell et al's method (Methods in Enzymology. 147: 407-414 (1987)). 3H-labeled proline (3 µCi/ml) was added to serum-free media to initiate culture. Immediately after culture initiation, a JNK inhibitor peptide (D-JNKI1, 0, 1, 2, and 5 mM, ALEXIS) was administered. At 72 hours after peptide administration, proteins in the culture supernatants were collected. Furthermore, only fractions that had been solubilized by collagen degrading enzymes were collected. 3H-labeled proline that had been incorporated for novel collagen synthesis was measured using a scintillation counter.

Results

Figure 5:
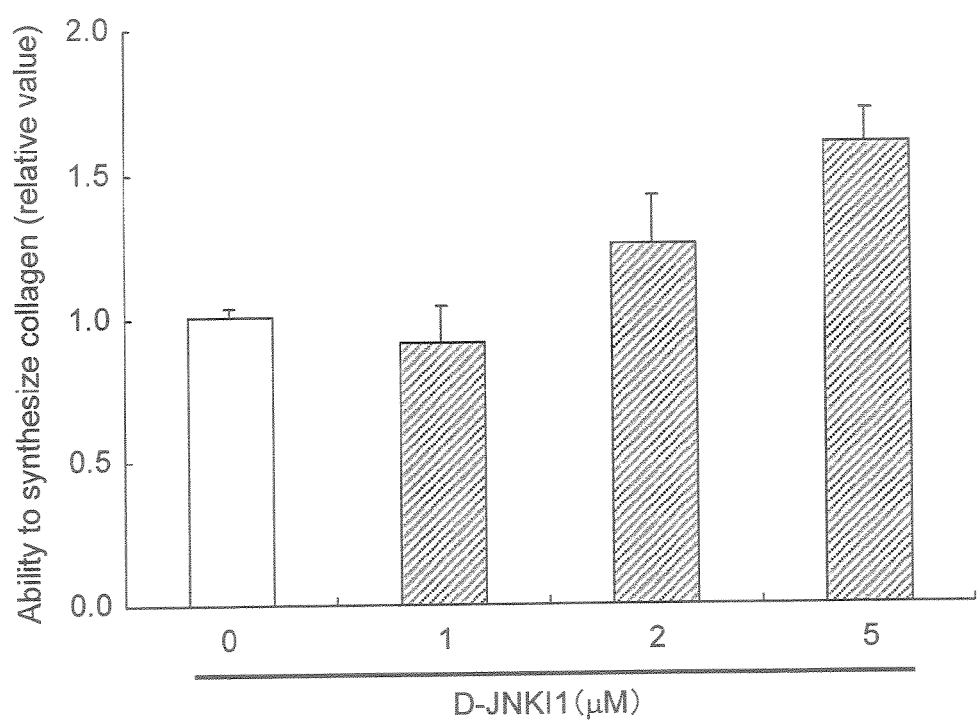
FIG. 5 is a graph showing the effect of a JNK inhibitor peptide of promoting ability to synthesize collagen in cultured cells.

The JNK inhibitor peptide D-JNKI1 promoted the ability to synthesize collagen in the cultured smooth muscle cells in a concentration-dependent manner (with 5 mM D-JNKI1 promoting the ability to a degree $1.6\pm0.1$ times ($p<0.01$) that of 0 mM D-JNKI1) (see FIG. 5).

Example 8

Effect of a JNK Inhibitor on Prolyl 4-hydroxylase

Methods

An experiment was conducted using a vascular smooth muscle cell primary culture system isolated from a rat aorta. A JNK inhibitor SP600125 (SP, 50 mM) was added to serum-free media. At 1 hour after SP addition, the cells were stimulated with TNF-α (R&D Systems, 10 ng/ml). At 24 hours after stimulation with TNF-α, the cells were harvested. Prolyl 4-hydroxylase expression was subjected to quantitative analysis at the mRNA level using the Northern blot method. Prolyl 4-hydroxylase (P4H) is one of important enzymes that is essential for collagen synthesis. Decreased level of P4H indicates lowered ability to synthesize collagen.

Results

Figure 6:
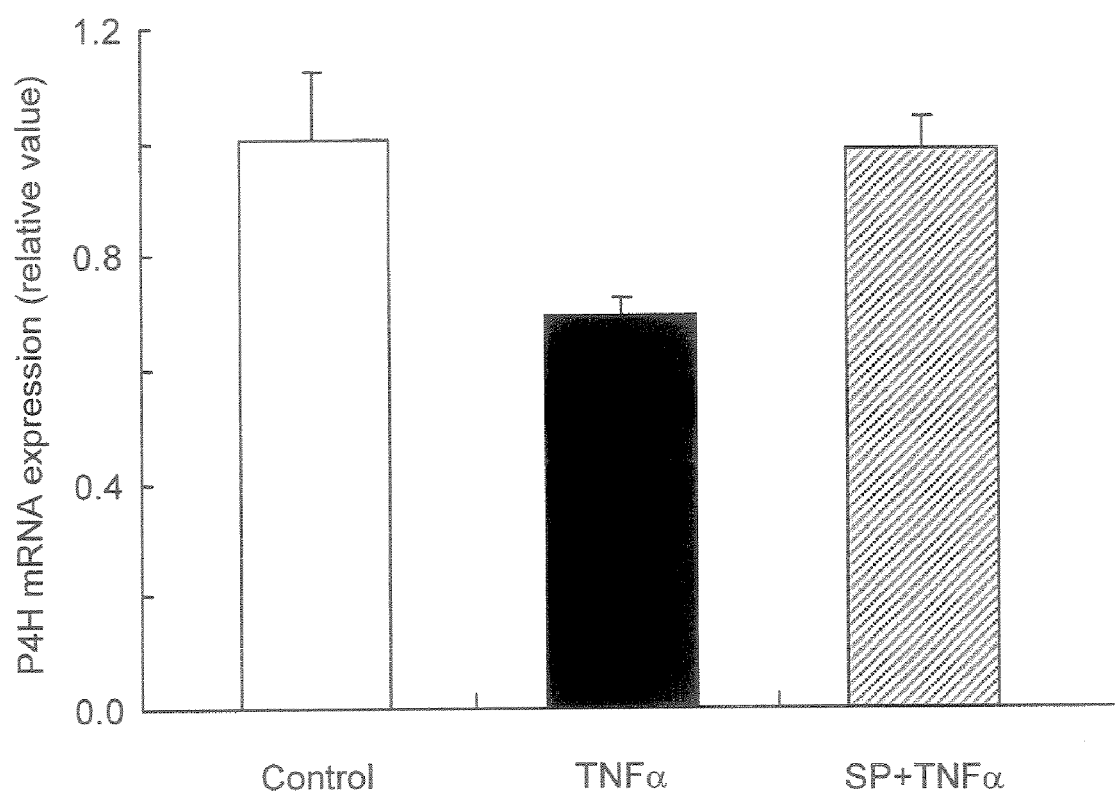
FIG. 6 is a graph showing the effect of a JNK inhibitor of enhancing prolyl 4-hydroxylase expression in cultured cells.

The expression level of prolyl 4-hydroxyiase in the cultured smooth muscle cells was decreased by stimulation with TNF-α infammatory cytokine. The JNK inhibitor SP600125 inhibited a decrease in prolyl 4-hydroxylase expression level and restored the ability to synthesize collagen ($p<0.05$) (see FIG. 6).

Example 9

Effect of a JNK Inhibitor Peptide on Lysyl Oxidase

Methods

An experiment was conducted using a vascular smooth muscle cell primary culture system isolated from a rat aorta. Serum deficiency state was created at the initiation of the experiment. JNK of cultured cells was activated by serum-deficiency stress. Immediately after the initiation of the experiment, a JNK inhibitor peptide (D-JNKI1, 5 mM, ALEXIS) was administered. D-TAT (5 mM, ALEXIS) was used as a control peptide. On day 6 after peptide administration, the cells were harvested. Lysyl oxidase expression was subjected to quantitative analysis at the mRNA level using the real time PCR method. Lysyl oxidase (LOX) is an enzyme essential for the maturation of collagen fiber or elastin fiber. Decreased level of LOX indicates lowered ability to synthesize collagen or elastin.

Results

Figure 7:
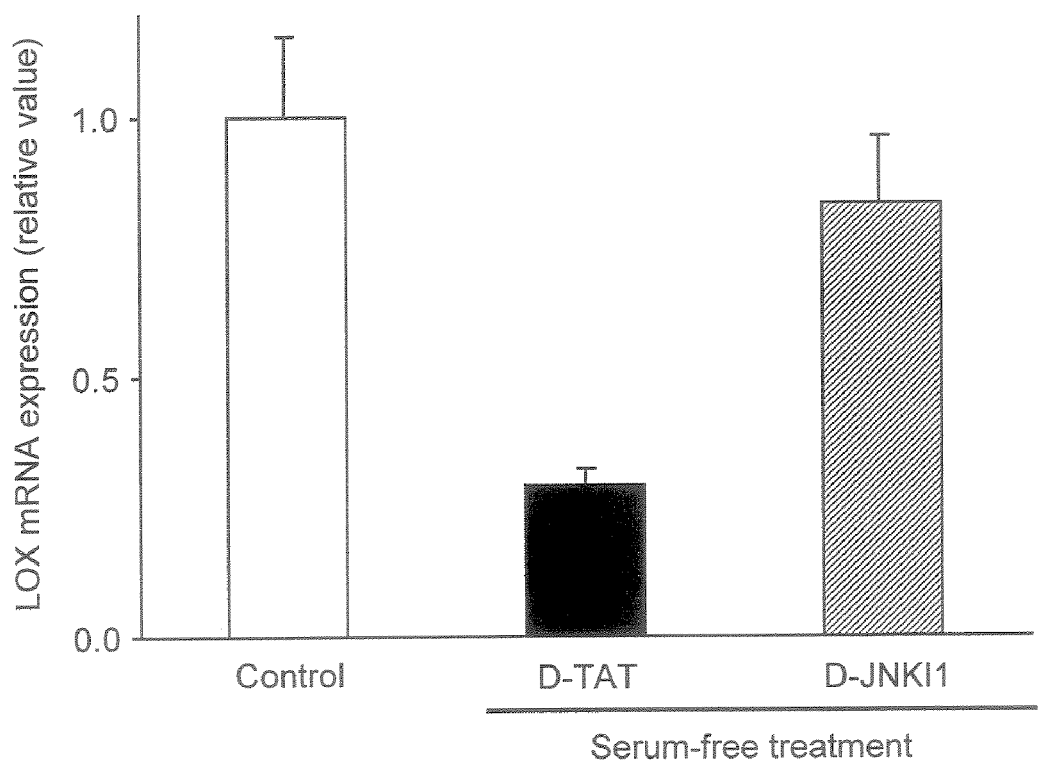
FIG. 7 is a graph showing the effect of a JNK inhibitor peptide of enhancing lysyl oxidase expression in cultured cells.

The expression level of lysyl oxidase in the cultured smooth muscle cells was decreased by stimulation with serum-deficiency stress. The JNK inhibitor peptide D-JNKI1 inhibited a decrease in lysyl oxidase expression level and restored the ability to synthesize collagen or elastin ($p<0.01$) (see FIG. 7).

Example 10

Analysis of the Ability of JNK2 Gene-Deficient Cells to Synthesize Extracellular Matrix Methods JNKs expressed in component cells of the aorta include JNK1 and JNK2 isoforms. An experiment was conducted using a vascular smooth muscle cell primary culture system isolated from the aorta of a JNK2 gene-deficient mouse (JNK2−/−). As control cells, cells isolated from a wild-type mouse having the same genetic background as that of the JNK2 gene-deficient mouse were used. These cells were separately harvested in a state of no stimulation. Lysyl oxidase (LOX) expression was subjected to quantitative analysis at the mRNA level using the real time PCR method. Alternatively, the enzyme activity of lysyl oxidase was determined. Lysyl oxidase is an enzyme essential for the maturation of collagen fiber or elastin fiber. Decreased level of lysyl oxidase indicates lowered ability to synthesize collagen or elastin. Furthermore, a cytokine TGF-β that is thought to integrally promote extracellular matrix synthesis was subjected to quantitative analysis at the protein expression level by the ELISA method.

Results

Figure 8:
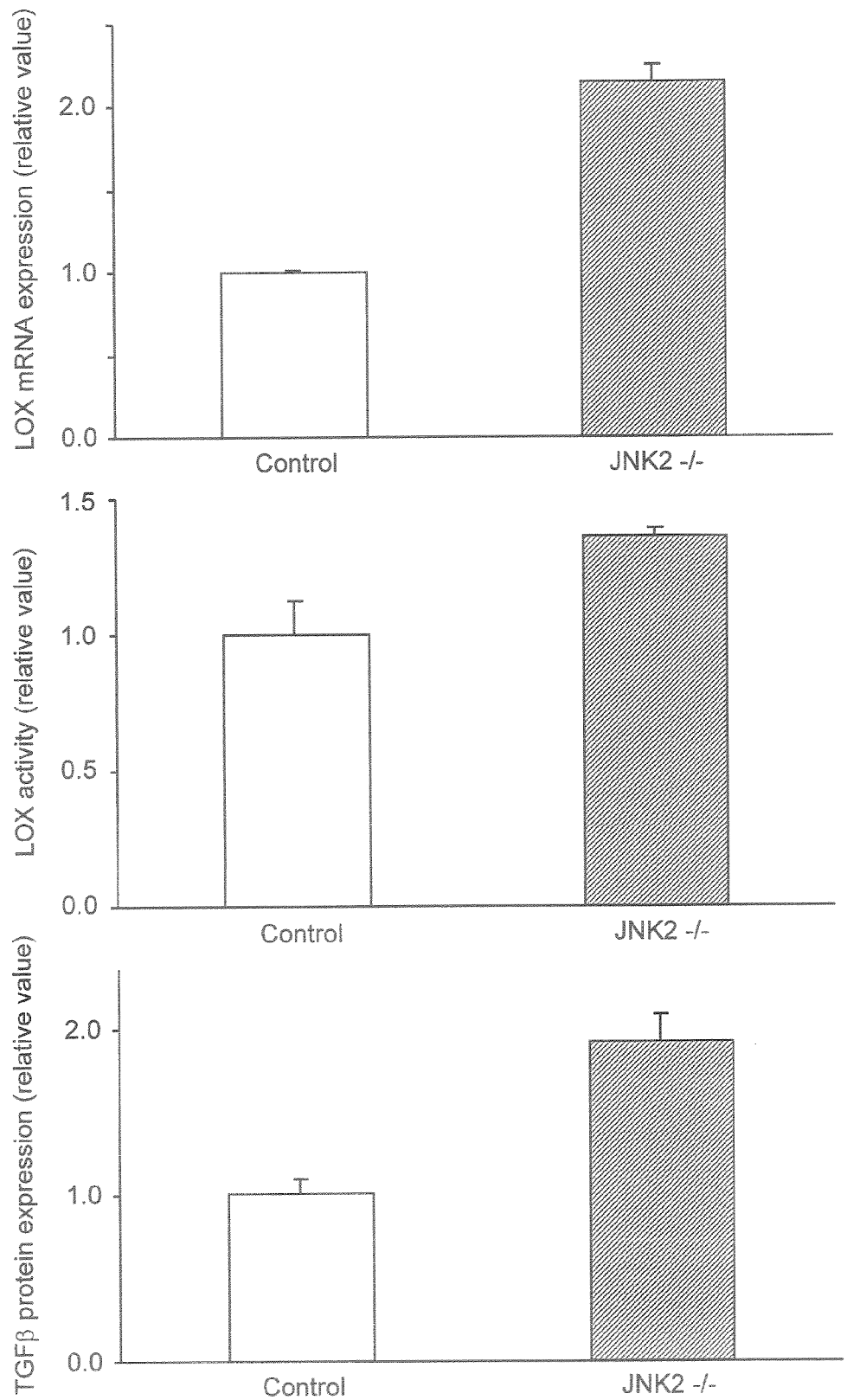
FIG. 8 is a graph showing the effect of JNK2-specific inhibition of promoting collagen or elastin synthesis in cultured cells.

The expression and enzyme activity levels of lysyl oxidase were significantly increased in JNK2-deficient cells (p<0.01). Moreover, TGF-β was also significantly increased in JNK2-deficient cells (p<0.01). Hence, the ability to synthesize collagen or elastin was promoted by JNK2-specific inhibition (see FIG. 8).

Example 11

Effect of a Suppression-Type JNK Variant on a Collagen Synthesis System

Methods

An experiment was conducted using a vascular smooth muscle cell primary culture system isolated from a rat aorta. To activate JNK, the cells were stimulated with oxidation stress using hydrogen peroxide ($H_2O_2$, 200 mM). Furthermore, to specifically suppress JNK, a recombinant adenovirus (Ad-JNK (APF)) expressing a suppression-type (dominant negative) JNK variant was prepared. A recombinant adenovirus (Ad-GFP) expressing GFP was used as a control. First, the cultured cells were stimulated with $H_2O_2$ and then harvested 24 hours later ($H_2O_2$ group). A group not subjected to any stimulation with $H_2O_2$ was used as a comparative control group (control group). Next, cultured cells that had been infected in advance with Ad-JNK (APF) or Ad-GFP were stimulated with $H_2O_2$ and then harvested 24 hours later ($H_2O_2$+APF group and $H_2O_2$+GFP group). A gene group that had shown changes in expression due to stimulation with $H_2O_2$ and a gene group that had shown changes in expression due to the effect of the suppression-type JNK variant were exhaustively analyzed by oligo DNA microarray (Affymetrix, RG-U34).

Results

As a result of exhaustive analysis, prolyl 4-hydroxylase (P4H), lysyl hydroxylase (PLOD), and lysyl oxidase (LOX) that are essential enzymes for collagen fiber synthesis were identified as enzymes whose expression level is lowered by activation of JNK due to stimulation with $H_2O_2$ and whose expression level is increased by the effect of the JNK variant of suppressing JNK. Specifically, the prolyl 4-hydroxylase expression level was lowered by stimulation with $H_2O_2$ to a level 0.62 times the level of the control group (based on the ratio of the level of the $H_2O_2$ group to that of the control group), but increased through suppression of JNK by Ad-JNK (APF) to a level 1.32 times the level of the $H_2O_2$+GFP group (based on the ratio of the level of the $H_2O_2$+APF group to that of the $H_2O_2$+GFP group). Furthermore, the lysyl hydroxylase expression level was lowered by stimulation with $H_2O_2$ to a level 0.76 times the level of the control group (based on the ratio of the level of the $H_2O_2$ group to that of the control group), but increased through suppression of JNK by Ad-JNK (APF) to a level 1.41 times the level of the $H_2O_2$+GFP group (based on the ratio of the level of the $H_2O_2$+APF group to that of the $H_2O_2$+GFP group). Furthermore, the lysyl oxidase expression level was lowered by stimulation with $H_2O_2$ to a level 0.87 times the level of the control group (the ratio of the level of the $H_2O_2$ group to that of the control group), but increased through suppression of JNK by Ad-JNK (APF) to a level 1.23 times the level of the $H_2O_2$+GFP group (based on the ratio of the level of the $H_2O_2$+APF group to that of the $H_2O_2$+GFP group). These results revealed that the suppression-type JNK variant enhances the expression of prolyl 4-hydroxylase, lysyl hydroxylase, and lysyl oxidase that are essential for collagen fiber synthesis. Particularly, lysyl oxidase is also essential for elastin fiber synthesis. Hence, it was shown that the suppression-type JNK variant enhances the synthesis system of collagen fiber and elastin fiber.

Example 12

JNK2-Specific Suppression Experiment Using Calcium Chloride-Treated Mouse Aneurysm Model Methods An abdominal aortic aneurysm model was generated by treating mice with calcium chloride according to Longo et al's method (J. Clin. Invest. 110: 625-632 (2002)). Specifically, the abdominal cavity of each 7-week-old male C57BL/6 mouse was opened, the infrarenal abdominal aorta was stimulated with 0.5 M calcium chloride for 15 minutes, and then the abdominal cavity was closed (Ca group: 11 mice). Aneurysms that gradually become dilated by week 6 are formed by this treatment. The aorta of each male C57BL/6 mouse of a sham surgery group (Na group: 5 mice) was treated with physiological saline. Furthermore, to verify the effect of JNK2-specific inhibition in the aneurysm model, the aorta of each JNK2 gene-deficient mouse (JNK2−/−, 7-week-old, male) was similarly subjected to impregnation treatment with 0.5 M calcium chloride (JNK2−/− group, 6 mice). Following 6 weeks of postoperative rearing, the mice were sacrificed. The maximum diameter of the infrarenal abdominal aorta and the aortic diameter of the suprarenal abdominal aorta not subjected to calcium treatment were measured.

Results

Figure 9:
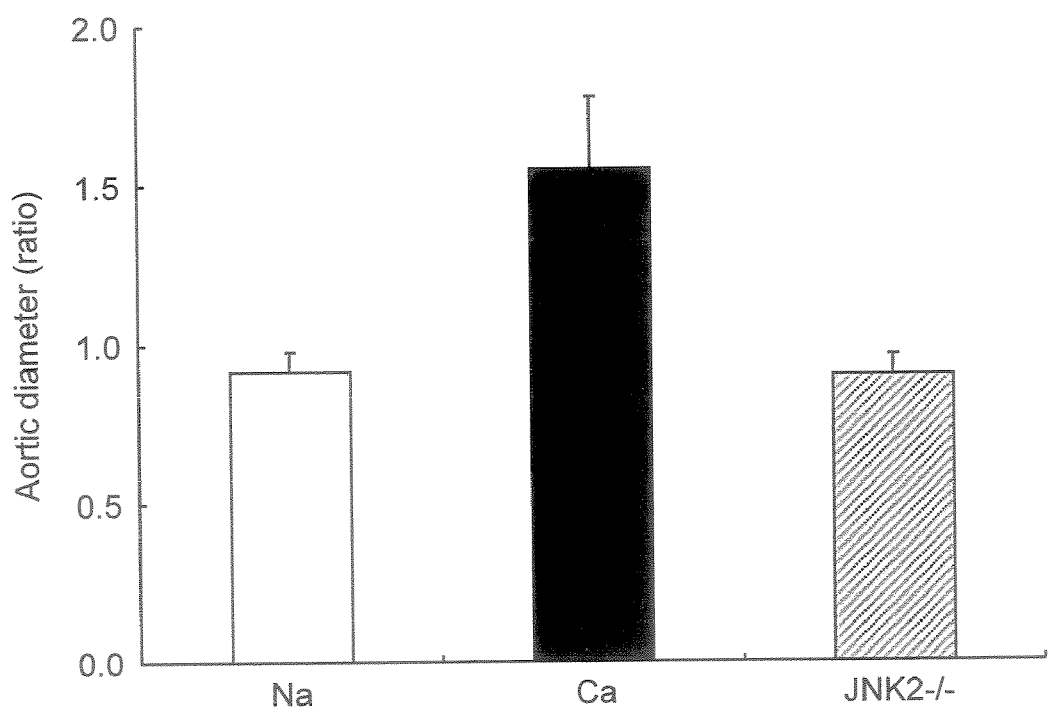
FIG. 9 is a graph showing the results of an experiment concerning aneurysm therapy using inhibition of JNK2 in a calcium chloride-treated mouse aneurysm model.

Diameters of the infrarenal abdominal aorta measured on week 6 after operation were: 0.67 mm±0.06 mm in the Na group; 1.15 mm±0.17 mm in the Ca group; and 0.62 mm±0.08 mm in the JNK2−/− group. Aortic diameters in the control group treated with calcium chloride were significantly increased compared with those of the sham surgery group, and aneurysm formation was observed in the control group. To eliminate the effect of individual differences between JNK2−/− mice and the mice of the Na and the Ca groups, the ratio of the maximum infrarenal aortic diameter to the suprarenal aortic diameter was calculated. As a result, the results were: 0.92±0.06 in the Na group; 1.55±0.23 in the Ca group; and 0.90±0.06 in the JNK2−/− group. Specifically, aneurysm formation induced by stimulation with calcium chloride was almost completely suppressed in the JNK2−/− group (Fisher's exact test: p<0.01). Based on the above results, it was demonstrated that aneurysm formation in calcium chloride-treated mice is inhibited by JNK2-specific suppression (see FIG. 9).

INDUSTRIAL APPLICABILITY

The present invention makes it possible to prevent and treat disorders of collagen or elastin metabolism. The drug of the present invention can be used as a prophylactic agent for suppressing aneurysmal progression in particular, or as a therapeutic agent for causing aneurysm regression. The drug can also be used as a drug for systemic administration (e.g., internal use or injection) or topical administration using a stentgraft or the like.

All publications, patents, and patent applications cited herein are incorporated herein by reference in their entirety.

The invention claimed is:

1. A method for treating vascular aneurysm by regressing the size of the aneurysm in an individual suffering from a vascular aneurysm, the method comprising administering a substance possessing c-Jun N-terminal Kinase (JNK) inhibitory activity to the individual to treat the vascular aneurysm, wherein:
   (a) the substance possessing JNK inhibitory activity is a substance that restores the ability to synthesize collagen or elastin;
   (b) the substance possessing JNK inhibitory activity is Anthra[1-9-cd]pyrazol-6(2H)-one (SP600125); and
   (c) the vascular aneurysm is an abdominal aortic aneurysm (AAA).

2. The method according to claim 1, wherein the substance possessing JNK inhibitory activity is administered in the form of an injection.

3. The method according to claim 1, wherein the substance possessing JNK inhibitory activity is administered in the form of an oral agent.

4. The method according to claim 1, wherein the substance possessing JNK inhibitory activity is administered in the form of an external remedy.

* * * * *